United States Patent
Konstandopoulos

(10) Patent No.: US 7,866,146 B2
(45) Date of Patent: Jan. 11, 2011

(54) EXHAUST GAS PURIFYING APPARATUS, EXHAUST GAS PURIFYING METHOD, AND PARTICULATE MATTER MEASURING METHOD

(75) Inventor: Athanasios G. Konstandopoulos, 45 Tselepi, Thessaloniki (GR) 54352

(73) Assignees: Ibiden Co., Ltd., Ogaki-shi (JP); Athanasios G. Konstandopoulos, Thessaloniki (GR)

( * ) Notice: Subject to any disclaimer, the term of this patent is extended or adjusted under 35 U.S.C. 154(b) by 451 days.

(21) Appl. No.: 11/852,043

(22) Filed: Sep. 7, 2007

(65) Prior Publication Data
US 2008/0087011 A1  Apr. 17, 2008

(30) Foreign Application Priority Data
Oct. 17, 2006 (EP) .................................. 06386030

(51) Int. Cl.
*F01N 3/02* (2006.01)
(52) U.S. Cl. ..................... 60/311; 60/274; 60/276; 60/287; 60/292; 60/297; 60/324
(58) Field of Classification Search ............ 60/276, 60/277, 288, 292, 297, 274, 287, 295, 311, 60/324, 286
See application file for complete search history.

(56) References Cited

U.S. PATENT DOCUMENTS

| | | | | |
|---|---|---|---|---|
| 4,633,706 A * | 1/1987 | Ito et al. | ............ | 73/23.33 |
| 4,835,964 A | 6/1989 | Kume et al. | | |
| 5,489,319 A * | 2/1996 | Tokuda et al. | ............ | 96/400 |
| 5,822,977 A * | 10/1998 | Fukuda et al. | ............ | 60/274 |
| 6,370,936 B1 | 4/2002 | Yamagishi et al. | | |
| 6,779,339 B1 * | 8/2004 | Laroo et al. | ............ | 60/297 |
| 7,021,048 B2 * | 4/2006 | Taylor et al. | ............ | 60/295 |
| 7,370,474 B2 * | 5/2008 | Minami | ............ | 60/295 |
| 7,484,357 B2 * | 2/2009 | Dollmeyer et al. | ............ | 60/274 |
| 2005/0103013 A1 * | 5/2005 | Brookshire et al. | ............ | 60/605.2 |
| 2007/0130923 A1 * | 6/2007 | Dye et al. | ............ | 60/295 |
| 2008/0087007 A1 | 4/2008 | Konstandopoulos | | |
| 2008/0087012 A1 | 4/2008 | Konstandopoulos | | |
| 2008/0087101 A1 | 4/2008 | Konstandopoulos | | |
| 2008/0098724 A1 | 5/2008 | Konstandopoulos | | |

FOREIGN PATENT DOCUMENTS

| | | |
|---|---|---|
| AT | 413887 B | 7/2006 |
| JP | 55-019934 | 2/1980 |
| JP | 60-242341 | 12/1985 |
| JP | 2005-240652 | 9/2005 |
| JP | 2005240652 A * | 9/2005 |

OTHER PUBLICATIONS

European Search Report, 06386030.8, mailed Mar. 21, 2007.

* cited by examiner

*Primary Examiner*—Binh Q Tran
(74) *Attorney, Agent, or Firm*—Ditthavong Mori & Steiner, P.C.

(57) ABSTRACT

An exhaust gas purifying apparatus includes a primary diesel particulate filter provided in an exhaust line of a diesel engine, a secondary exhaust line branched from the exhaust line from an upstream side of the primary diesel particulate filter, and a secondary diesel particulate filter provided in the secondary exhaust line. The secondary diesel particulate filter has a soot storage capacity smaller than the soot storage capacity of the primary diesel particulate filter. The apparatus further includes a differential pressure measuring part for measuring a differential pressure between an inlet and an outlet of the secondary diesel particulate filter.

19 Claims, 20 Drawing Sheets

EXHAUST GAS

EXHAUST GAS PURIFYING APPARATUS, EXHAUST GAS PURIFYING METHOD, AND PARTICULATE MATTER MEASURING METHOD

CROSS-REFERENCE TO RELATED APPLICATIONS

The present application claims priority under 35 U.S.C. §119 to European Patent Application No. 06386030.8 filed on Oct. 17, 2006. The contents of this European Patent application are incorporated herein by reference in their entirety.

BACKGROUND OF THE INVENTION

1. Field of the Invention

The present invention relates to exhaust gas purifying apparatuses, exhaust gas purifying method, and particulate matter measuring method.

2. Discussion of the Background

Conventionally, a diesel particulate filter of porous ceramic has been used for collecting particulate matter (PM) primarily of C (carbon) emitted from a diesel engine. With such a diesel particulate filter (DPF), there occurs gradual deposition of particulate matter with continual use thereof, and thus, it has been practiced in the art of exhaust gas purifying apparatus that uses a diesel particulate filter to remove the deposited particulate matter by causing a burning process inside the diesel particulate filter periodically and regenerate the diesel particulate filter.

It is preferable that such regeneration of the diesel particulate filter is conducted during the operation of the diesel engine, without replacing or dismounting the filter, and thus, it is practiced in the art to carry out fuel injection in the state that the piston is moving down in the cylinder following combustion to form a high temperature gas (post injection process). Thereby, the deposited particulate matter is burned with the high temperature gas thus formed.

FIG. 1 shows the overall construction of an exhaust gas purifying system of a diesel engine equipped with a diesel particulate filter according to a related art of the present invention.

With the conventional exhaust gas purifying system explained with reference to FIG. 1, it should be noted that such regeneration of filter is conducted each time the vehicle has traveled a predetermined mileage such as 500 km, over the duration of 10 minutes, for example.

In the case the filter regeneration by way of post injection has been conducted impartially, the regeneration is carried out irrespective of actual amount of collection of the particulate matter in the filter. Thus, in order to ensure that there occurs no excessive deposition of the particulate matter in the filter, there is a need to set the interval of filter regeneration to be shorter than what is actually needed for the sake of safety.

On the other hand, there is a known construction of carrying out regeneration of the diesel particulate filter 12B by way of post injection as shown in FIG. 3, in which a differential pressure $\Delta P$ is measured between the upstream side and downstream side of the diesel particulate filter 12B and the post injection is carried out when the foregoing differential pressure $\Delta P$ has reached a predetermined value. Reference should be made to the U.S. Pat. No. 6,952,920.

Further, U.S. Pat. No. 5,651,248 describes the construction that uses, in addition to the diesel particulate filter, a detection filter and evaluates the amount of the particulate matter collected in the detection filter by measuring the electric resistance. According to this technology, the particulate matter collected by the diesel particulate filter and the particulate matter collected by the detection filter are subjected to burning by using a heater when the detected resistance has decreased below a predetermined value. With this, regeneration of filter is achieved.

The contents of U.S. Pat. Nos. 6,952,920 and 5,651,248 are incorporated herein by reference in their entirety.

SUMMARY OF THE INVENTION

In a first aspect, an exhaust gas purifying apparatus of the present invention includes a primary diesel particulate filter provided in an exhaust line of a diesel engine; a secondary exhaust line branched from the exhaust line from an upstream side of the primary diesel particulate filter; a secondary diesel particulate filter provided in the secondary exhaust line, the secondary diesel particulate filter having the soot storage capacity smaller than the soot storage capacity of the primary diesel particulate filter; and a differential pressure measuring part measuring a differential pressure between an inlet and an outlet of the secondary diesel particulate filter.

In another aspect, an exhaust gas purifying method of the present invention that uses an exhaust gas purifying apparatus including: a primary diesel particulate filter provided in an exhaust line of a diesel engine; a secondary exhaust line branched from the exhaust line from an upstream side of the primary diesel particulate filter; a secondary diesel particulate filter provided in the secondary exhaust line, the secondary diesel particulate filter having a soot storage capacity smaller than the soot storage capacity of the primary diesel particulate filter; and a differential pressure measuring part measuring a differential pressure between an inlet port and an outlet port of the secondary diesel particulate filter, the exhaust gas purifying method including the steps of:

(A) measuring a differential pressure caused across the secondary diesel particulate filter, a temperature of an exhaust gas in the secondary exhaust line, and a flow rate of the exhaust gas;

(B) calculating the mass of particulate matter collected by the secondary diesel particulate filter per unit time from the differential pressure, the temperature and the flow rate of the exhaust gas obtained in the step (A);

(C) calculating the concentration of the particulate matter in the exhaust gas from the mass of particulate matter collected by the secondary diesel particulate filter per unit time obtained in the step (B);

(D) calculating the mass of the particulate matter flowed into the primary diesel particulate filter from the concentration of the particulate matter in the exhaust gas obtained in the step (C) and further from a state of engine operation or a gas flow rate to the primary diesel particulate filter;

(E) judging whether or not the mass of the particulate matter collected by the primary diesel particulate filter has exceeded a predetermined threshold from the mass of the particulate matter collected by the primary diesel particulate filter obtained in the step (D) and a collection efficiency of the primary diesel particulate filter; and (F) executing regeneration of the primary diesel particulate filter in the event the mass of the diesel particulate matter collected by the primary diesel particulate filter has exceeded the predetermined threshold.

In another aspect, a particulate matter measuring method of the present invention that uses a particulate matter sensor, the particulate matter sensor including: a PM detection filter provided in a gas line branched from an exhaust line of a diesel engine from an upstream side of a diesel particulate filter provided in the exhaust line, the PM detection filter having a soot storage capacity smaller than the soot storage capacity of the diesel particulate filter; and a differential pressure measuring part measuring a differential pressure between an inlet port and an outlet port of the PM detection filter, the particulate matter measuring method including the steps of:

(A) measuring a differential pressure caused across the PM detection filter, a temperature of an exhaust gas in the gas line, and a flow rate of the exhaust gas in the gas line;

(B) calculating the mass of particulate matter collected by the PM detection filter per unit time from the differential pressure, the temperature and the flow rate of the exhaust gas obtained in the step (A);

(C) calculating the concentration of the particulate matter in the exhaust gas from the mass of particulate matter collected by the PM detection filter per unit time obtained in the step (B);

(D) calculating the mass of the particulate matter flowed into the primary diesel particulate filter from the concentration of the particulate matter in the exhaust gas obtained in the step (C) and further from a state of engine operation or a gas flow rate to the primary diesel particulate filter.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
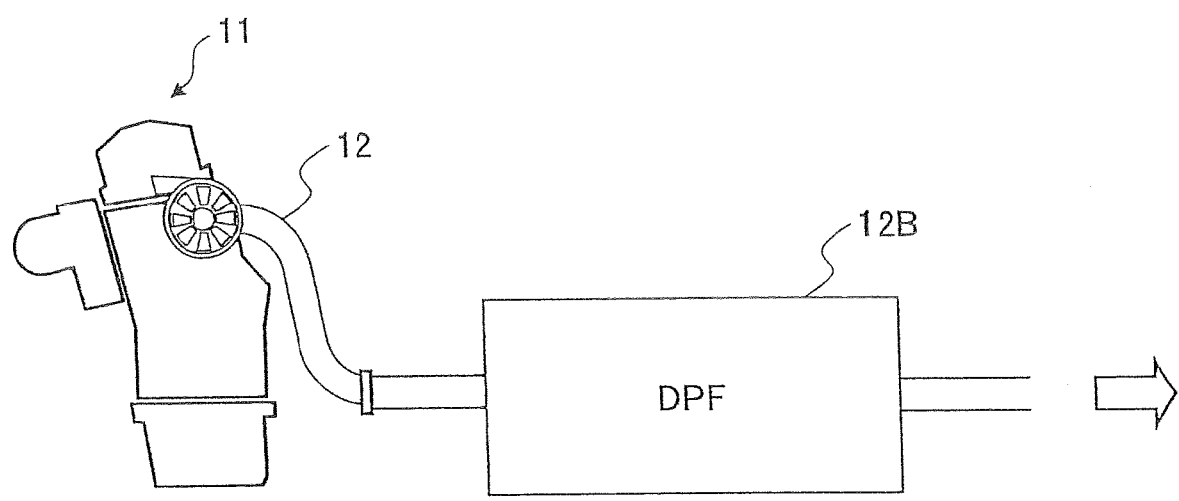
FIG. 1 is a diagram showing an overall engine system that uses a conventional exhaust gas purifying apparatus.

The embodiments will now be described with reference to the accompanying drawings, wherein like reference numerals designate corresponding or identical elements throughout the various drawings.

According to a preferred embodiment of the present invention, there is provided an exhaust gas purifying apparatus including: a primary diesel particulate filter provided in an exhaust line of a diesel engine; a secondary exhaust line branched from the exhaust line at an upstream side of the primary diesel particulate filter; a secondary diesel particulate filter provided in the secondary exhaust line, the secondary diesel particulate filter having a capacity smaller than a capacity of the primary diesel particulate filter; and a differential pressure measuring part measuring a differential pressure between an inlet and an outlet of the secondary diesel particulate filter.

Preferably, the secondary exhaust line further includes a flow meter or equivalent meter (e.g. a gas velocity meter).

Preferably, the secondary exhaust line further includes a temperature measuring part.

Preferably, the secondary diesel particulate filter includes a heater.

Preferably, the exhaust gas purifying apparatus further includes a valve for maintaining a flow rate of the exhaust gas in the secondary exhaust line at a predetermined value.

According to a preferred embodiment of the present invention, there is provided an exhaust gas purifying method that uses an exhaust gas purifying apparatus, the exhaust gas purifying apparatus including: a primary diesel particulate filter provided in an exhaust line of a diesel engine; a secondary exhaust line branched from the exhaust line from an upstream side of the primary diesel particulate filter; a secondary diesel particulate filter provided in the secondary exhaust line, the secondary diesel particulate filter having a soot storage capacity smaller than the soot storage capacity of the primary diesel particulate filter; and a differential pressure measuring part measuring a differential pressure between an inlet port and an outlet port of the secondary diesel particulate filter, wherein the exhaust gas purifying method includes the steps of: (A) measuring a differential pressure caused across the secondary diesel particulate filter, a temperature of an exhaust gas in the secondary exhaust line, and a flow rate of the exhaust gas; (B) calculating the mass of particulate matter collected by the secondary diesel particulate filter per unit time from the differential pressure, the temperature and the flow rate of the exhaust gas obtained in the step (A); (C) calculating the concentration of the particulate matter in the exhaust gas from the mass of particulate matter collected by the secondary diesel particulate filter per unit time obtained in the step (B); (D) calculating the mass of the particulate matter flowed into the primary diesel particulate filter from the concentration of the particulate matter in the exhaust gas obtained in the step (C) and further from a state of engine operation or a gas flow rate to the primary diesel particulate filter; (E) judging whether or not the mass of the particulate matter collected by the primary diesel particulate filter has exceeded a predetermined threshold from the mass of the particulate matter collected by the primary diesel particulate filter obtained in the step (D) and the collection efficiency of the primary diesel particulate filter; and (F) executing regeneration of the primary diesel particulate filter in the event the mass of the diesel particulate matter collected by the primary diesel particulate filter has exceeded the predetermined threshold.

Preferably, the exhaust gas purifying method further includes the step of regenerating the secondary diesel particulate filter, regeneration of the secondary diesel particulate filter being executed independently to regeneration of the primary diesel particulate filter in the case when a mass of particulate matter collected in the secondary diesel particulate filter has exceeded a predetermined value.

Preferably, the step of regenerating the secondary diesel particulate filter is executed, after the step (A), by a first process that includes the step (B), and wherein the step of regenerating the primary diesel particulate filter is executed, after the step (B) of the first process, by a second process that includes the steps (C) and (D).

Preferably, the step of regenerating the secondary diesel particulate filter is executed, after the step (A), by a first process that includes the step (B), and wherein the step of regenerating the primary diesel particulate filter is executed, after the step (A), by a second process that includes the steps (B) to (D), wherein the first process and the second process are executed in parallel.

Preferably, the step (B) calculates the amount of soot load of the particulate matter collected in the secondary diesel particulate filter according to an equation of the form $$\Delta P = \text{function (Flow, Temperature, Soot load, Geometry)}$$

with a preferred example shown below (although other expressions can be also employed) according to which the thickness W[m] of a layer of the particulate matter collected in the secondary diesel particulate filter is calculated according to $$\Delta P = \frac{\mu Q}{2 V_{trap}} (\alpha + W_s)^2 \left[ \frac{W_s}{K_w \alpha} + \frac{1}{2 K_{SOOT}} \ln\left(\frac{\alpha}{\alpha - 2W}\right) + \frac{4FL^2}{3}\left(\frac{1}{(\alpha - 2W)^4} + \frac{1}{\alpha^4}\right) \right] + \frac{\rho Q^2 (\alpha + W_s)^4}{V_{trap}^2} \left[ \frac{\beta W_s}{4} + 2\varsigma \left[\frac{L}{\alpha}\right]^2 \right]$$

wherein $\Delta P$ represents the differential pressure [Pa], $\mu$ represents a kinetic viscosity coefficient, Q represents the flow rate of the exhaust gas in the second diesel particulate filter represented in terms of [m³/h], $\alpha$ represents an edge length of a cell in the secondary diesel particulate filter, $\rho$ represents a specific gravity of the exhaust gas, $V_{trap}$ represents a filter volume of the secondary diesel particulate filter, Ws represents a wall thickness of the secondary diesel particulate filter, Kw represents a well permeability of the secondary diesel particulate filter, $K_{soot}$ represents a permeability of the layer of the particulate matter collected in the second diesel particulate filter, F is a numerical coefficient (=28.454), L represents an effective filter length of the second diesel particulate filter, $\beta$ represents the Forchheimer coefficient of a porous wall of the second diesel particulate filter, $\varsigma$ represents the inertial loss coefficient of the exhaust gas entering and exiting the secondary diesel particulate filter, and further obtains a mass $m_{soot}$ [g] of the particulate matter collected in the secondary diesel particulate filter according to an equation $$W = \frac{\alpha - \sqrt{\alpha^2 - \frac{m_{soot}}{N_{cells} \times L \times \rho_{soot}}}}{2}$$

wherein $N_{cells}$ represents an aperture number of the cell at an inlet side thereof, and $\rho_{soot}$ represents a density of the collected particulate matter.

Preferably, the step (C) obtains a concentration $PM_{conc}$ [g/m³] of the particulate matter in the exhaust gas by an equation $$PM[\text{g/h}] = PM_{conc}[\text{g/m}^3] \times Q2[\text{m}^3/\text{h}]$$

wherein Q2 [m³/h] represents a flow rate of the exhaust gas passing through the secondary diesel particulate filter, PM [g/h] represents the mass of the particulate matter deposited per unit time.

Preferably, the step (D) obtains the amount ($PM_{enter\,full\,filter}$ [g/h]) of the particulate matter flowed into the primary diesel particulate filter by an equation $$PM_{enter\,full\,filter}[\text{g/h}] = PM_{conc}[\text{g/m}^3] \times Q1[\text{m}^3/\text{h}]$$

where $PM_{conc}$ [g/m³] represents a concentration of particulate matter in the exhaust gas.

According to a preferred embodiment of the present invention, there is provided a particulate matter measuring method that uses a particulate matter sensor, the particulate matter sensor including: a PM detection filter provided in a gas line branched from an exhaust line of a diesel engine at an upstream side of a diesel particulate filter provided in the exhaust line, the PM detection filter having a capacity smaller than a capacity of the diesel particulate filter; and a differential pressure measuring part measuring a differential pressure between an inlet port and an outlet port of the PM detection filter, the particulate matter measuring method including the steps of: (A) measuring a differential pressure caused across the PM detection filter, a temperature of an exhaust gas in the gas line, and a flow rate of the exhaust gas in the gas line; (B) calculating the mass of particulate matter collected by the PM detection filter per unit time from the differential pressure, the temperature and the flow rate of the exhaust gas obtained in the step (A); (C) calculating the concentration of the particulate matter in the exhaust gas from the mass of particulate matter collected by the PM detection filter per unit time obtained in the step (B); (D) calculating the mass of the particulate matter flowed into the primary diesel particulate filter from the concentration of the particulate matter in the exhaust gas obtained in the step (C) and further from a state of engine operation or a gas flow rate to the primary diesel particulate filter Preferably, the step of calculating the mass of the particulate matter collected by the PM detection filter is executed, after the step (A), by a first process that includes the step (B), and wherein the step of calculating the mass of the particulate matter flowed into the diesel particulate filter is executed, after the step (B) of the first process, by a second process that includes the steps (C) and (D).

Preferably, the step of calculating the mass of the particulate matter collected by the PM detection filter is executed, after the step (A), by a first process that includes the step (B), and wherein the step of calculating the mass of the particulate matter flowed into the diesel particulate filter is executed, after the step (A), by a second process that includes the steps (B)-(D), wherein the first process and the second process are executed in parallel.

Preferably, the step (B) calculates the amount of soot load of the particulate matter collected in the secondary diesel particulate filter according to an equation of the form ΔP=function (Flow, Temperature, Soot load, Geometry)

with a preferred example shown below (although other expressions can be also employed) according to which the thickness W[m] of a layer of the particulate matter collected in the secondary diesel particulate filter is calculated according to $$\Delta P = \frac{\mu Q}{2V_{trap}}$$

$$(\alpha + W_s)^2 \left[ \frac{W_s}{K_w \alpha} + \frac{1}{2K_{SOOT}} \ln\left(\frac{\alpha}{\alpha - 2W}\right) + \frac{4FL^2}{3}\left(\frac{1}{(\alpha - 2W)^4} + \frac{1}{\alpha^4}\right) \right] +$$

$$\frac{\rho Q^2 (\alpha + W_s)^4}{V_{trap}^2}\left[\frac{\beta W_s}{4} + 2\zeta\left[\frac{L}{\alpha}\right]^2\right]$$

wherein ΔP represents the differential pressure [Pa], μ represents a kinetic viscosity coefficient, Q represents the flow rate of the exhaust gas in the PM detection filter represented in terms of [m³/h], α represents an edge length of a cell in the PM detection filter, ρ represents a specific gravity of the exhaust gas, $V_{trap}$ represents a filter volume of the PM detection filter, Ws represents a wall thickness of the PM detection filter, Kw represents a well permeability of the PM detection filter, $K_{soot}$ represents a permeability of the layer of the particulate matter collected in the PM detection filter, F is a numerical coefficient (=28.454), L represents an effective filter length of the PM detection filter, β represents the Forchheimer coefficient of a porous wall of the PM detection filter, ç represents the inertial loss coefficient of the exhaust gas entering and exiting the PM detection filter, and further obtains a mass $m_{soot}$ [g] of the particulate matter collected in the PM detection filter according to an equation $$W = \frac{\alpha - \sqrt{\alpha^2 - \frac{m_{soot}}{N_{cells} \times L \times \rho_{soot}}}}{2}$$

wherein $N_{cells}$ represents an aperture number of the cell at an inlet side thereof, and $\rho_{soot}$ represents a density of the collected particulate matter.

Preferably, the step (C) obtains a concentration $PM_{conc}$ [g/m³] of the particulate matter in the exhaust gas by an equation $PM[g/h] = PM_{conc}[g/m^3] \times Q2[m^3/h]$ wherein Q2 [m³/h] represents a flow rate of the exhaust gas passing through the PM detection filter, PM [g/h] represents the mass of the particulate matter deposited per unit time in the PM detection filter.

Preferably, the step (D) obtains the amount ($PM_{enter\,full\,filter}$ [g/h]) of the particulate matter flowed into the primary diesel particulate filter by an equation $PM_{enter\,full\,filter}[g/h] = PM_{conc}[g/m^3] \times Q1[m^3/h]$ where $PM_{conc}$ [g/m³] represents a concentration of particulate matter in the exhaust gas.

Referring to FIG. 1, a diesel engine 11 has an exhaust line 12, wherein there is provided a diesel particulate filter 12B in the exhaust line 12 for collecting the particulate matter contained in the exhaust gas and emitted from the diesel engine 11.

Figure 2A:
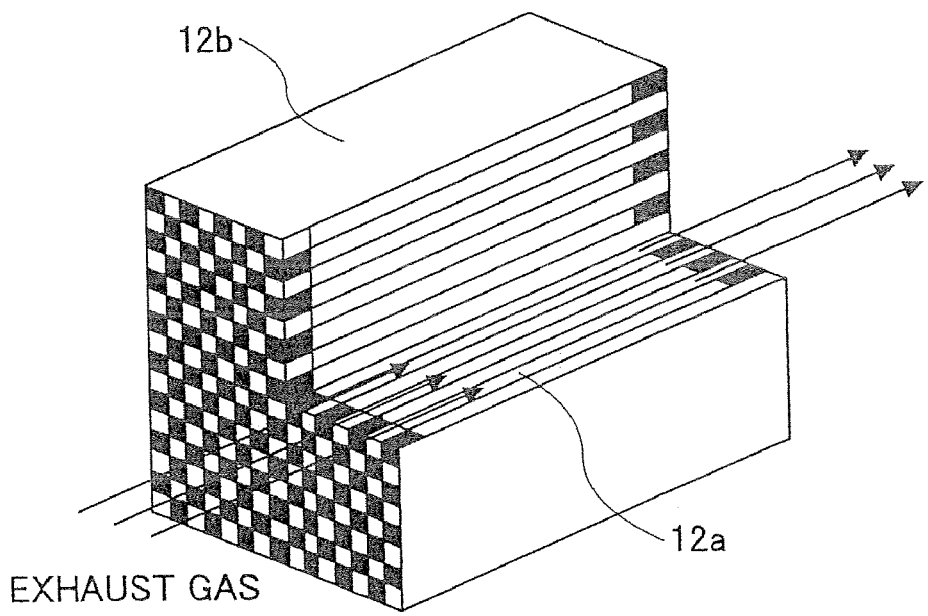
FIG. 2A is a diagram showing a schematic construction of a diesel particulate filter.
Figure 2B:
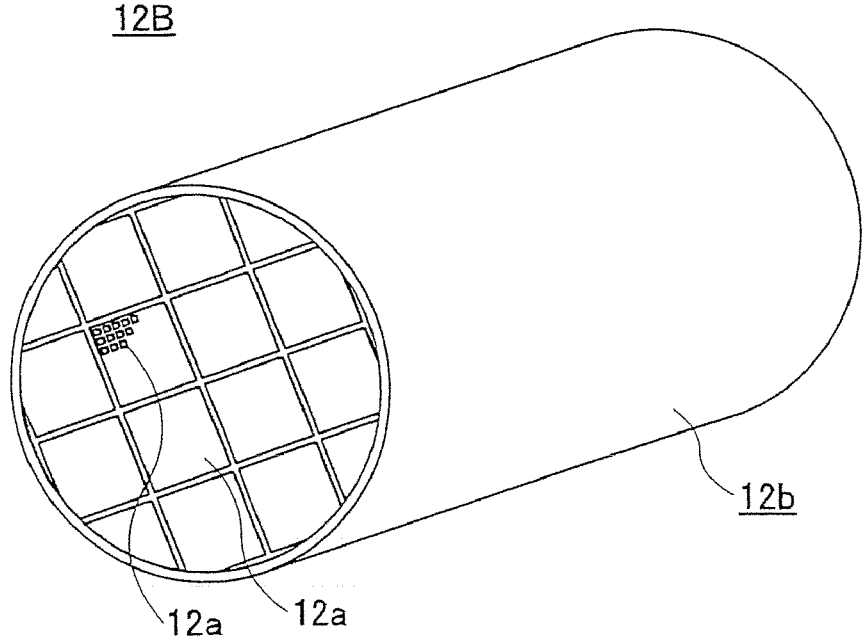
FIG. 2B is a diagram showing a constituting element of the diesel particulate filter.

FIG. 2A shows the outline of the diesel particulate filter 12B while FIG. 2B shows an element that constitutes the diesel particulate filter.

The diesel particulate filter 12B is formed of a filter unit 12A of a porous ceramic, typically of SiC, wherein there are formed a large number of gas passages 12a in the filter unit 12A so as to extend from one end to the other end thereof with a cross-section of 1 mm×1 mm, for example.

Thereby, the diesel particulate filter 12B is formed by binding plural filter units (filter elements) 12A by a seal material (adhesion layer) and machining the peripheral part thereof such that the filter 12B as a whole has a cylindrical form. Further, the peripheral surface of the filter 12B is covered by a seal material (coating layer). There may be a case in which only one unit 12A is used in the diesel particulate filter 12B.

Figure 2C:
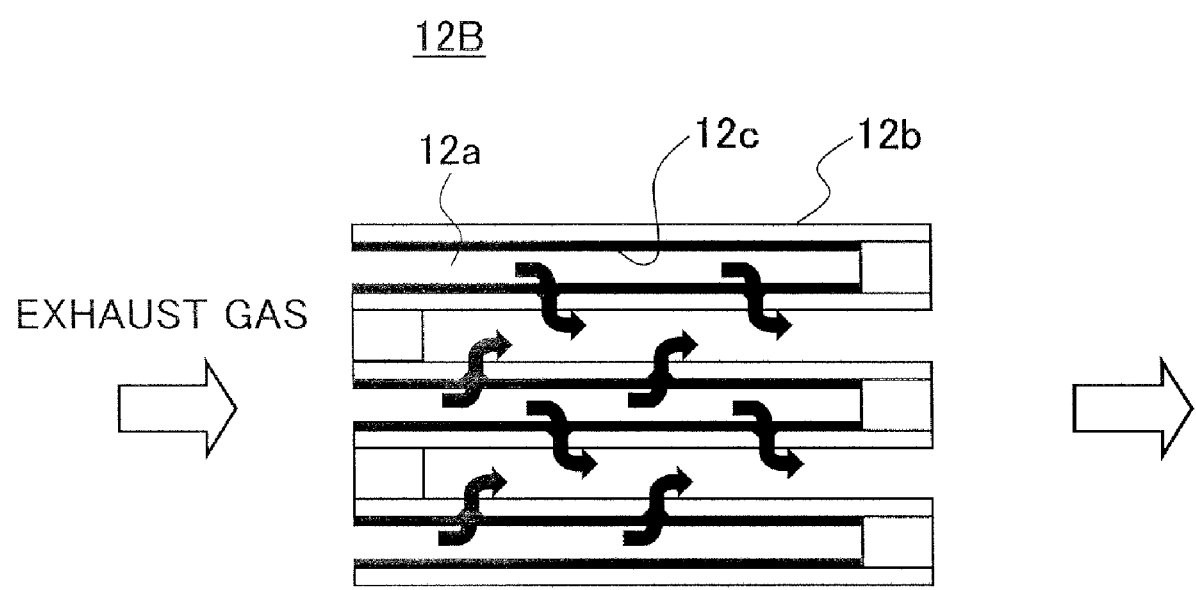
FIG. 2C is a diagram showing the operational principle of the diesel particulate filter.

FIG. 2C shows the principle of the diesel particulate filter 12B.

Figure 2D:
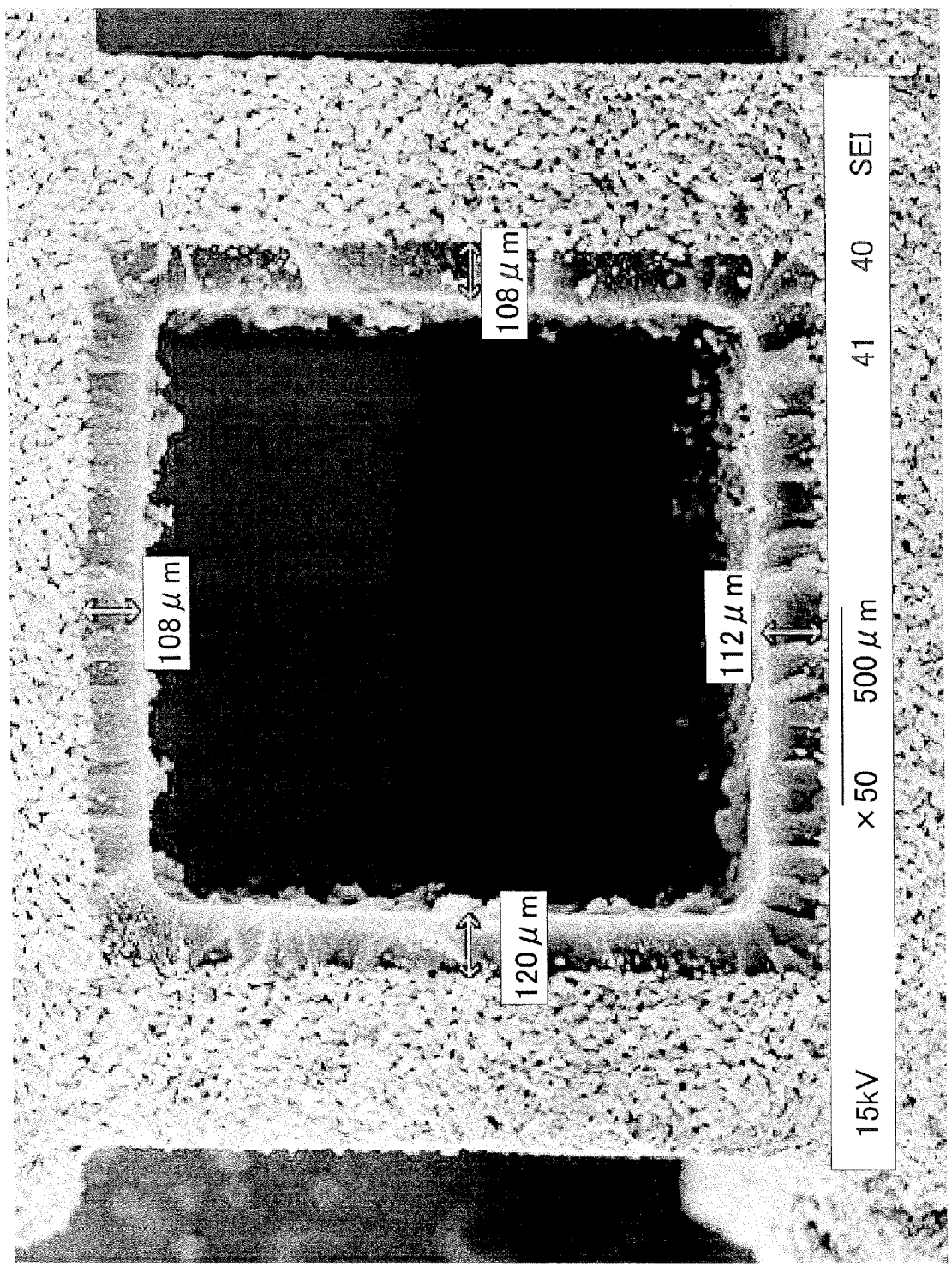
FIG. 2D is a diagram showing the state of the particulate matter collected by the diesel particulate filter.

As shown schematically in FIG. 2C, the plural gas passages 12a have their upstream ends or downstream ends closed alternately with regard to the direction of the exhaust gas flow from the engine, and the exhaust gas introduced to one such gas passage 12a passes to an adjacent gas passage by way of penetration through the porous member 12b of the filter 12B. Thereby, the particulate matter contained in the exhaust gas is collected by the porous member 12b as the exhaust gas penetrates therethrough, and there is caused deposition of the particulate matter 12c on the porous member 12b in the form of layer as shown in FIG. 2D.

Because the diesel particulate filter 12B thus causes deposition of the particulate matter contained in the exhaust gas therein, there is a need of regenerating the filter with suitable timing by conducting a regeneration process (burning of the deposited particulate matter), as described previously.

Figure 3:
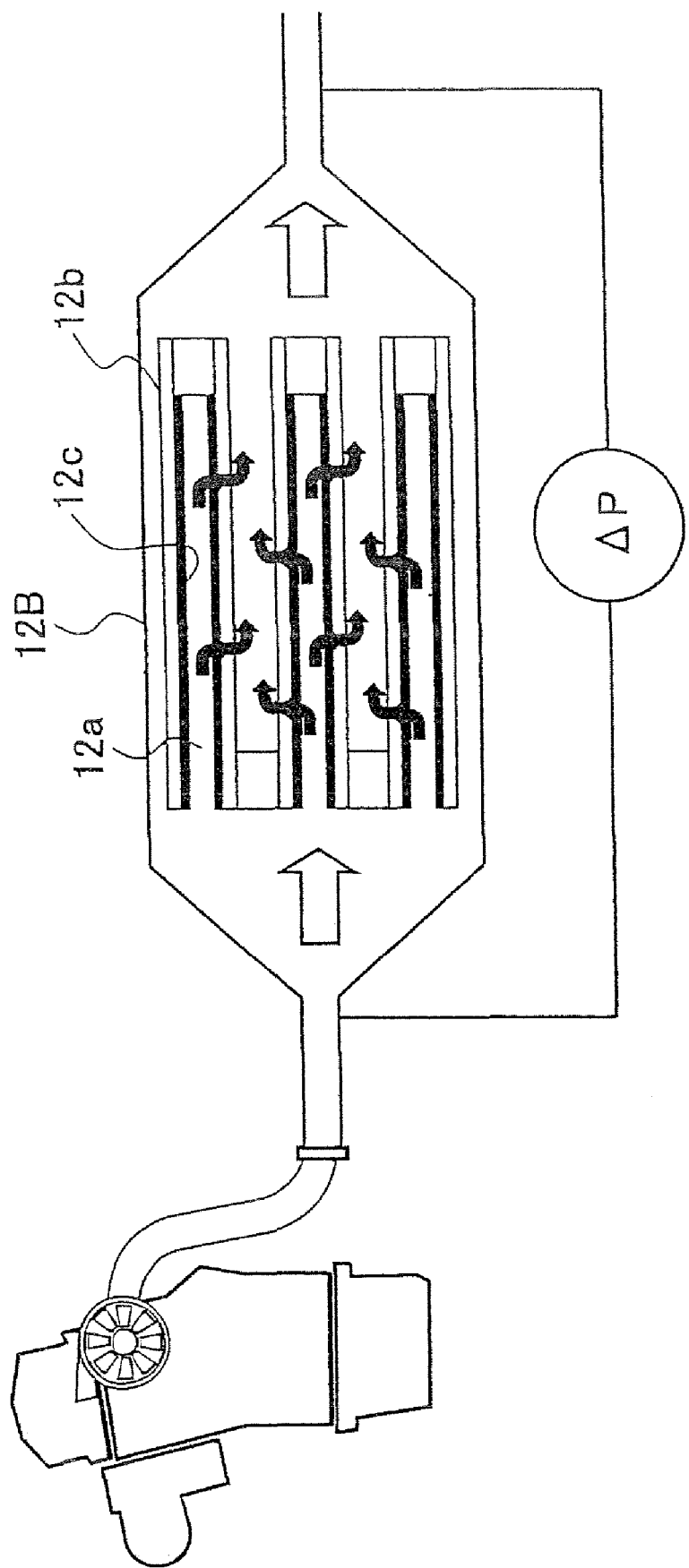
FIG. 3 is a diagram showing the overall construction of a conventional engine system that uses an exhaust gas purifying apparatus according to a related art of the present invention.

According to the conventional construction of FIG. 3, the regeneration of the diesel particulate filter 12B is carried out only when the differential pressure between the upstream side and the downstream side has reached the predetermined value, and unnecessary post injection process is suppressed. Thereby, the fuel efficiency of the vehicle driven with the diesel engine is improved.

Figure 4A:
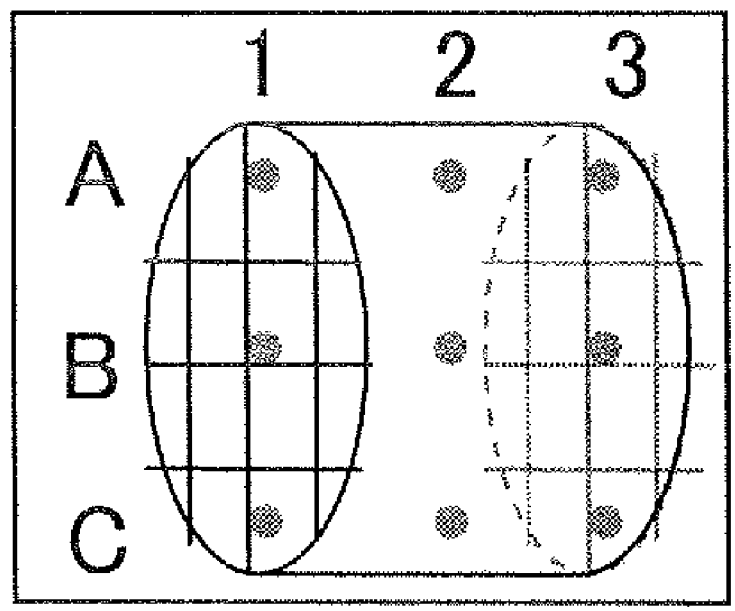
FIG. 4A is a diagram explaining the problem with the exhaust gas purifying apparatus of FIG. 3.
Figure 4A:
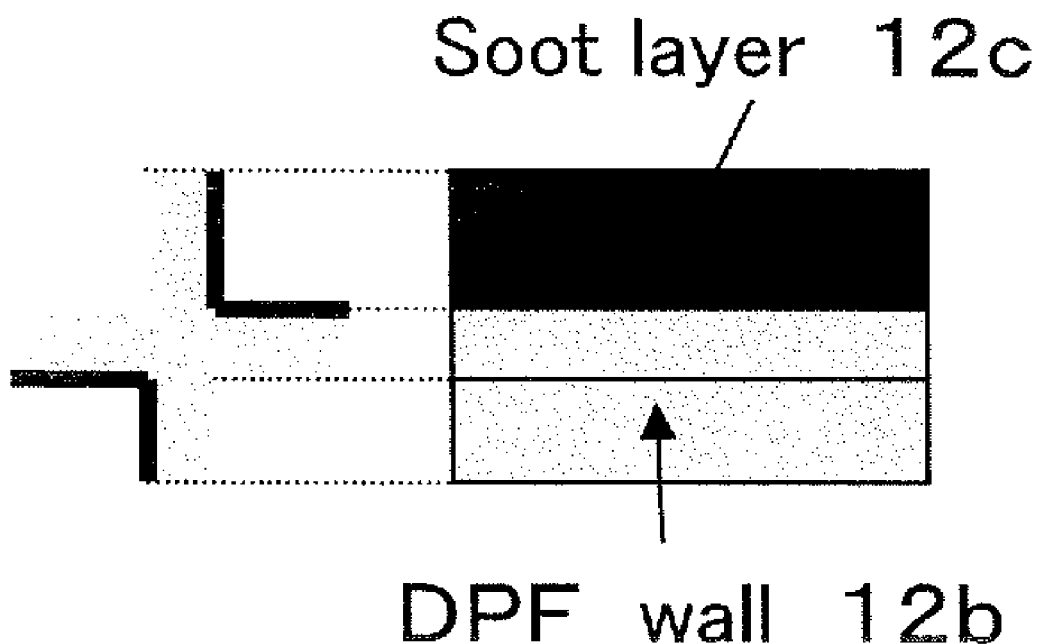
Figure 4B:
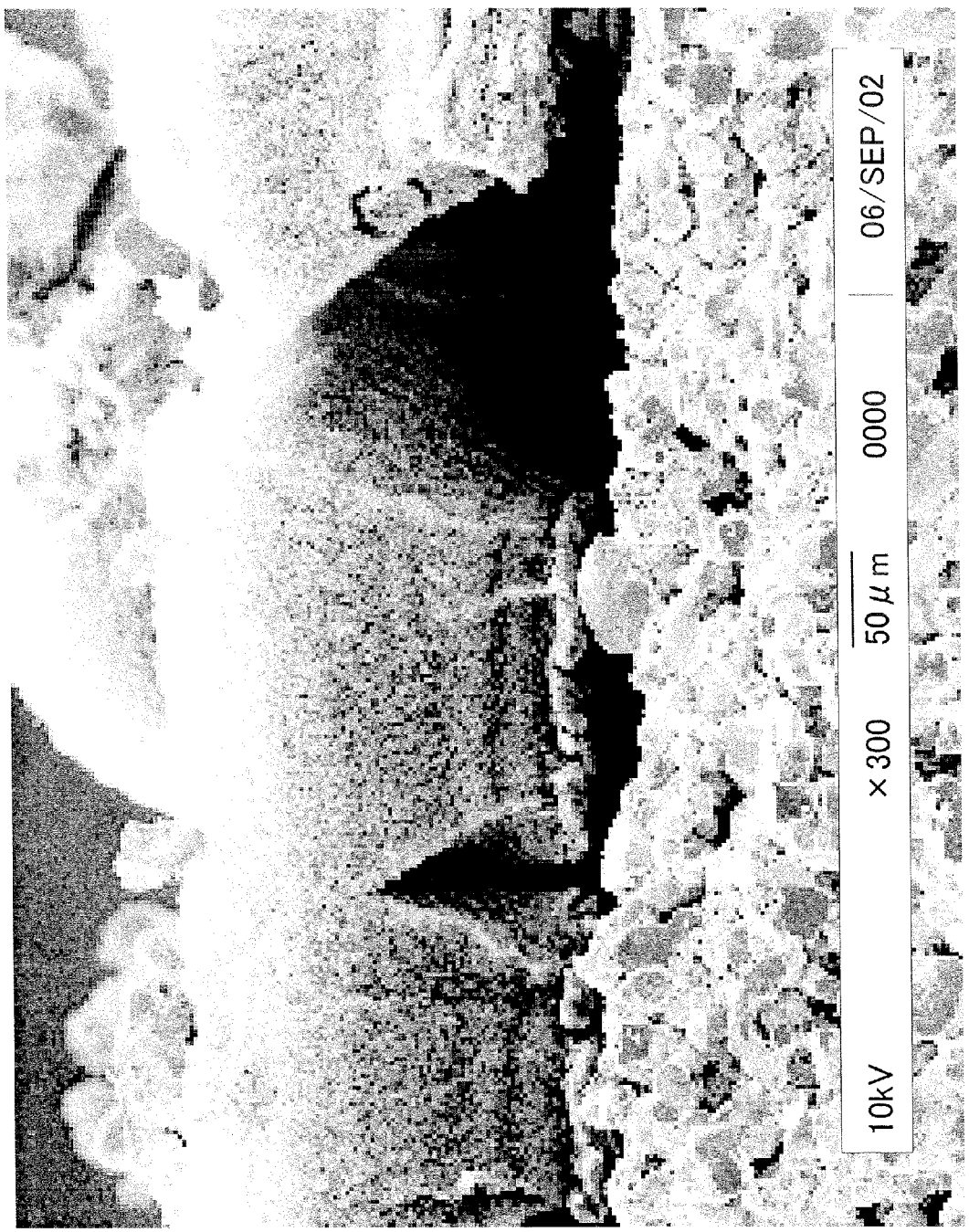
FIG. 4B is a diagram of collected particulate matter at location A1 in FIG. 4A.
Figure 4C:
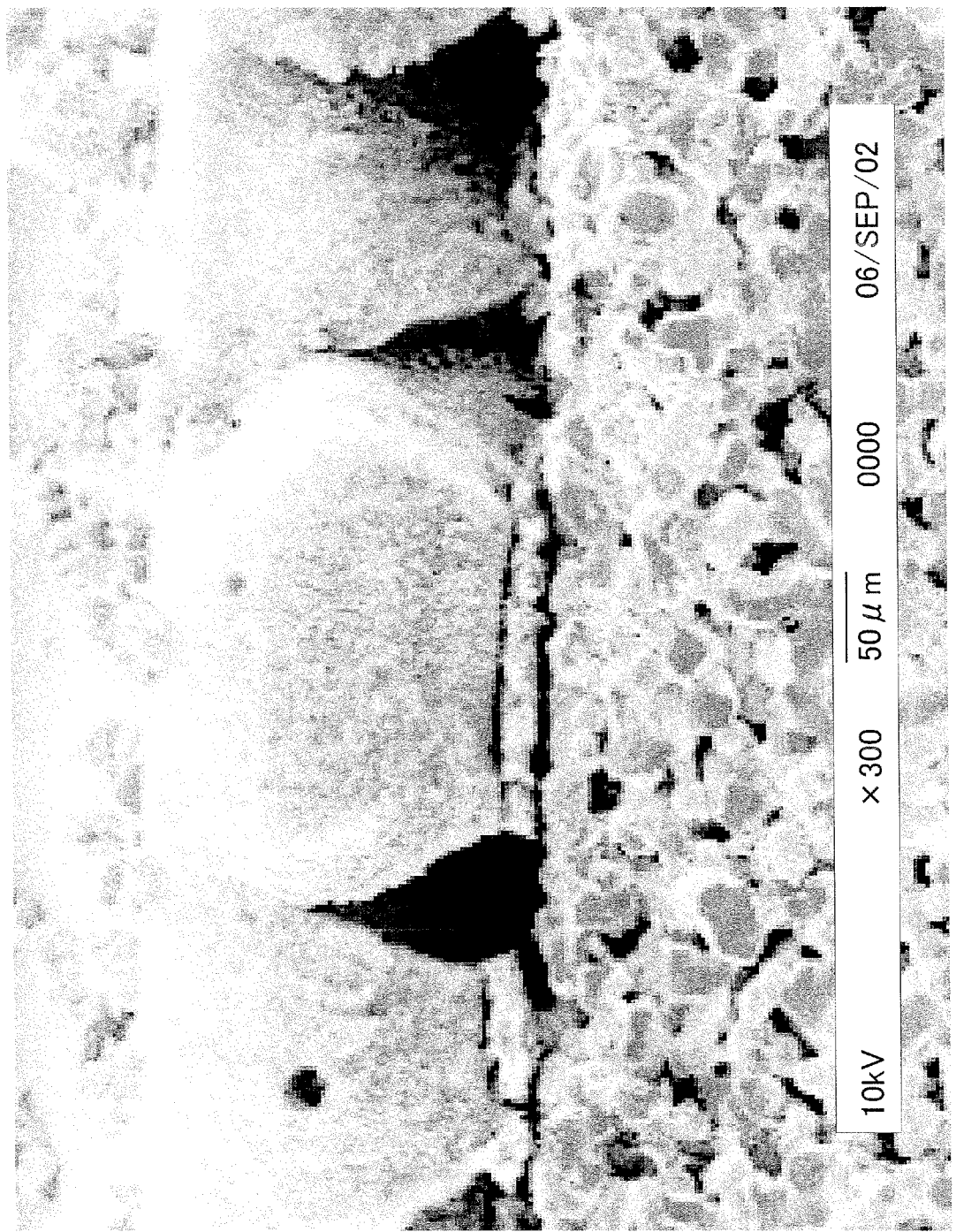
FIG. 4C is a diagram of collected particulate matter at location B2 in FIG. 4A.
Figure 4D:
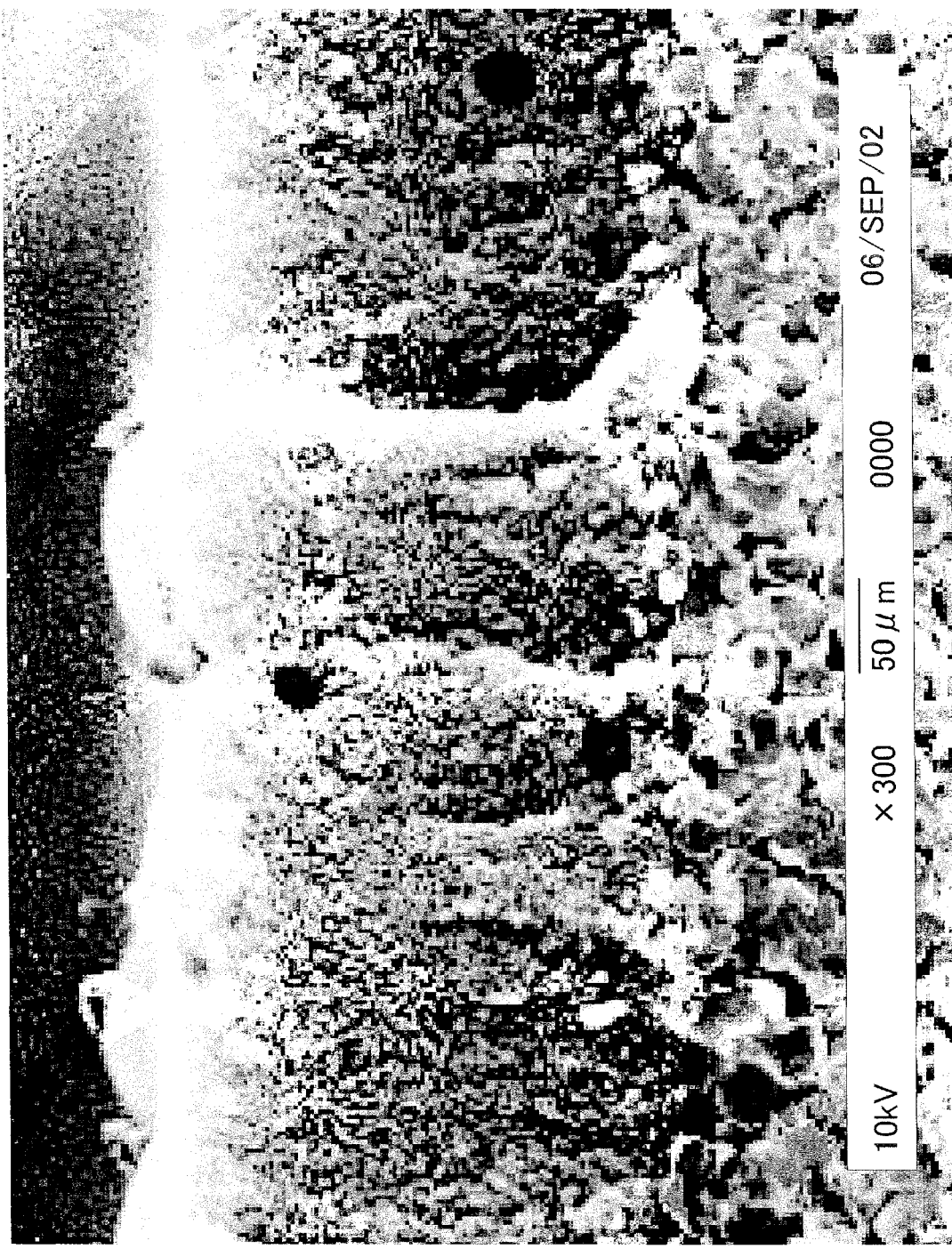
FIG. 4D is a diagram of collected particulate matter at location C3 in FIG. 4A.

Unfortunately, collection of the particulate matter in the diesel particulate filter 12B is not uniform. As shown in FIG. 4A, there is a difference of density or thickness in the collected particulate matter depending on the locations (A,1) (shown in FIG. 4B), (B,1), (C,1), (A,2), (B,2)(shown in FIG. 4C), (C,2), (A,3), (B,3), (C,3)(shown in FIG. 4D) in the filter 12B.

Further, it can be seen that there is formed a cavity in the layer of the deposited particulate matter, wherein such a cavity formed in the layer of particulate matter provides as a local passage of exhaust gas. Existence of such a cavity indicates occurrence of uncontrolled burning in the collected particulate matter and indicates further that there has been caused local burning in the collected particulate matter.

Figure 5A:
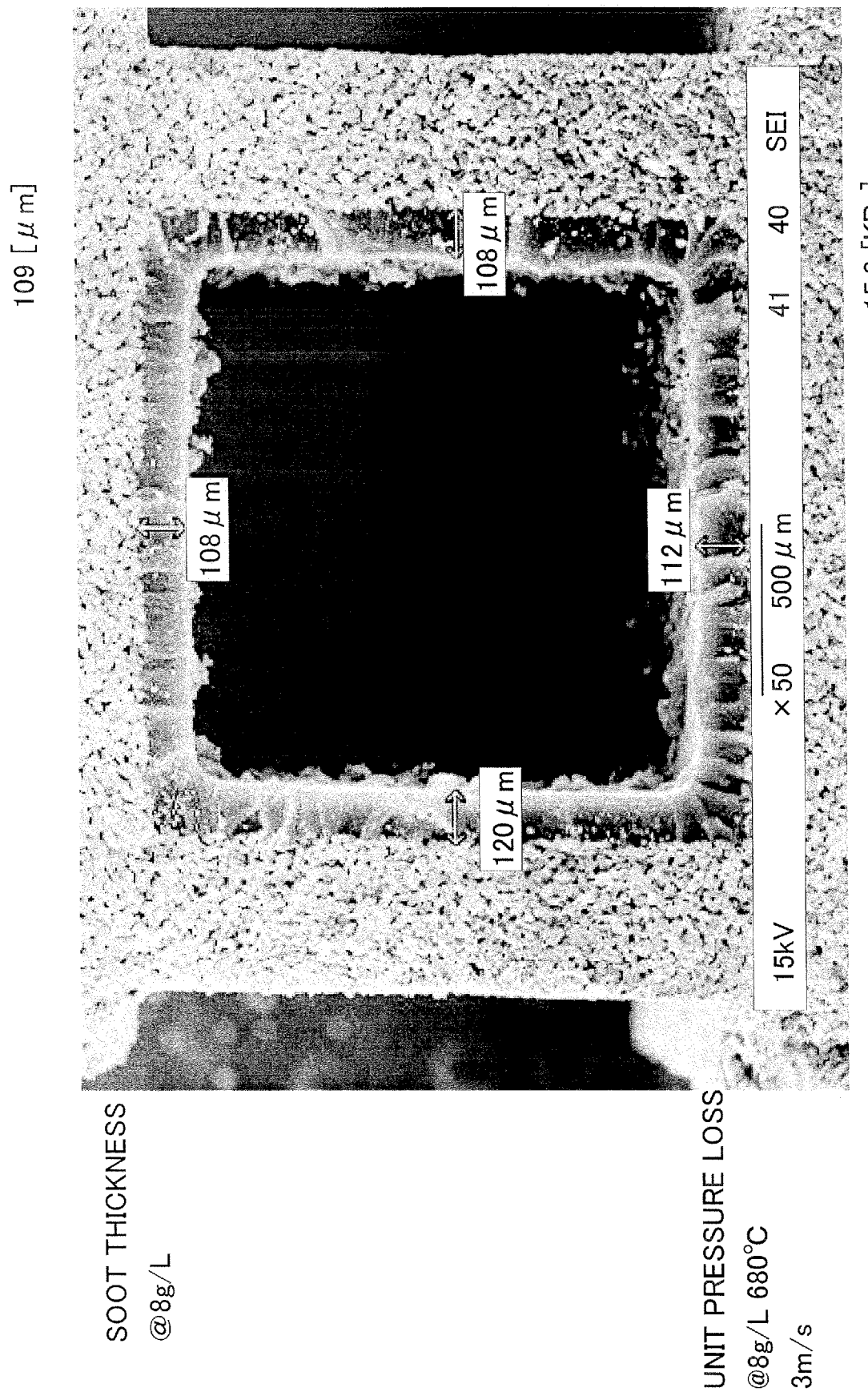
FIGS. 5A, 5B, and 5C are other diagrams explaining the problem of the exhaust gas purifying apparatus of FIG. 3.
Figure 5B:
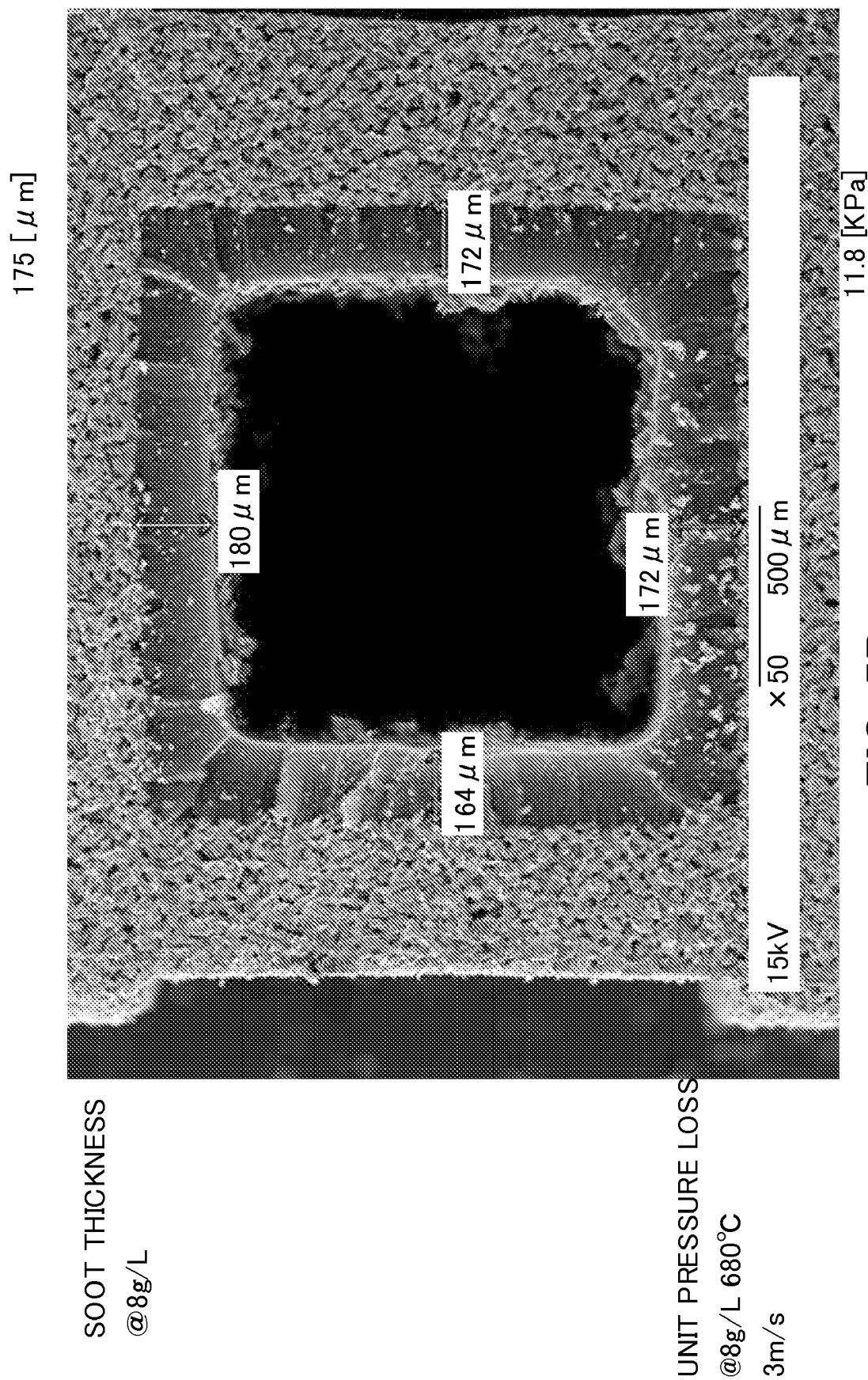
Figure 5C:
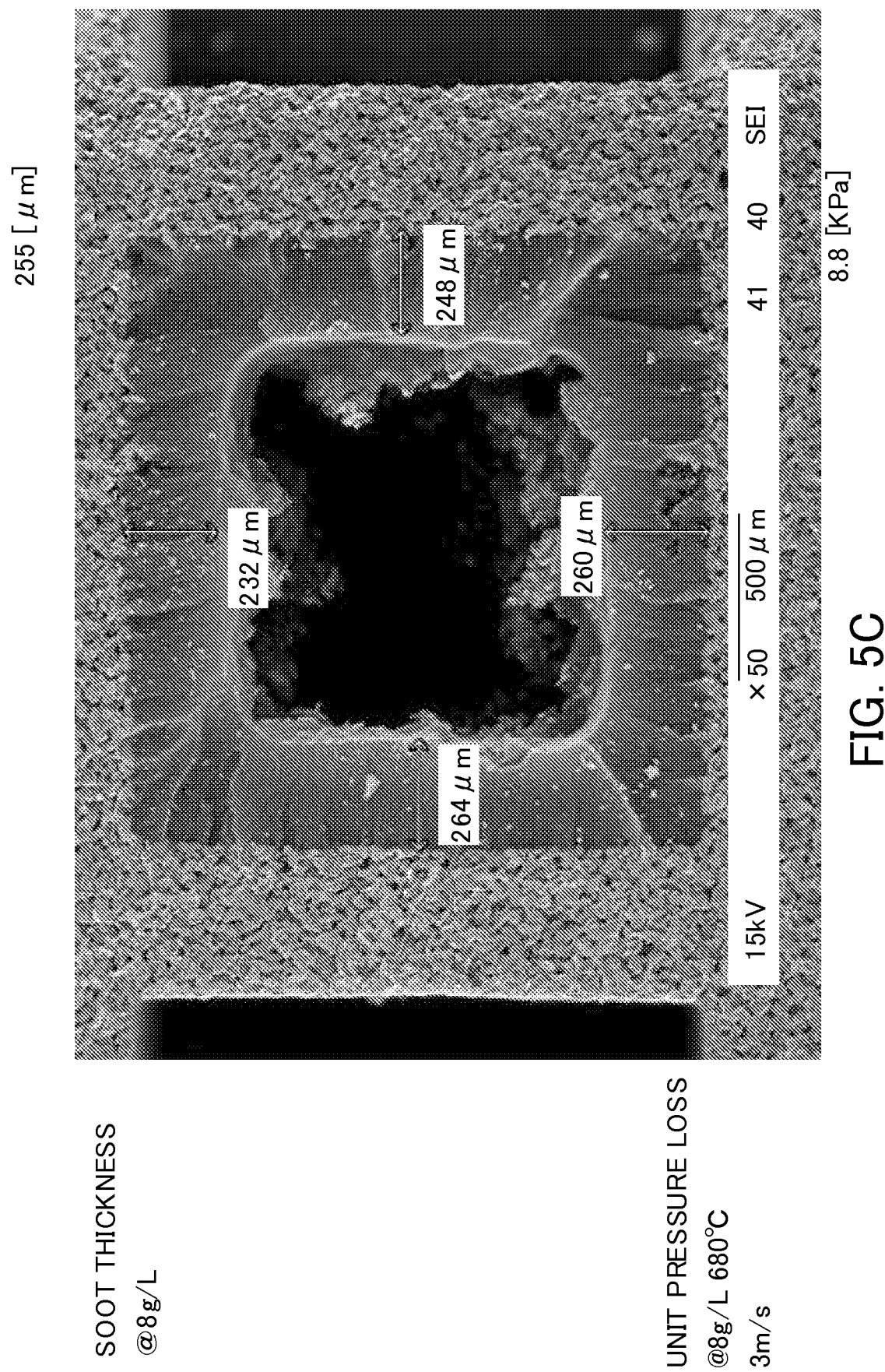

Further, as shown in FIGS. 5A, 5B, and 5C, the density of the collected particulate matter can take different values even when the deposition amount of the particulate matter is identical. FIGS. 5A, 5B, and 5C show that there is caused a large variation in the differential pressure according to the change of the thickness, even when the deposition amount is identical. In the examples of FIGS. 5A, 5B, and 5C, for example, it should be noted that the deposition amount of the particulate matter is 8 g/L throughout. In spite of this, it can be seen in FIG. 5A, 5B, and 5C that the differential pressure has changed from 15.3 kPa to 8.8 kPa when the thickness of the collected particulate matter has changed from 109 μm to 255 μm. Thus, it can be seen that there is caused about twice as large difference in the differential pressure.

Thus, when such non-uniform deposition or local cavity formation is caused in the particulate matter 12c collected in the conventional construction of FIG. 3, there can be caused an error of as much as ±50% with regard to the evaluation of the actually deposited particulate matter and the differential pressure ΔP, with regard to theoretical calculation values. As a result of such an error, there is caused a large deviation in the relationship between the amount of the actually deposited particulate and the timing of regeneration. Further, in view of the fact that the exhaust gas pressure and the exhaust gas flow rate change with engine load or engine revolution, it is extremely difficult with the construction of FIG. 3 to detect the deposition amount of the particulate matter in the diesel particulate filter 12B precisely.

On the other hand, this U.S. Pat. No. 5,651,248 has a drawback in that, in addition to the problem that the construction thereof becomes complex because of the need of providing a heater in the diesel particulate filter, there occurs electric power consumption at the time of regeneration of the diesel particulate filter. In order to save the electric power consumption at the time of filter regeneration, the technology of U.S. Pat. No. 5,651,248 selects the timing of executing the filter regeneration such that the regeneration operation is conducted at the time the temperature of the diesel particulate filter is higher than a predetermined temperature, except for the case in which the diesel particulate filter is in the critical state with regard to the deposition of the particulate matter and it is inevitable to carry out regeneration immediately. As a result, there is imposed a restriction on the timing of regenerating operation of the detection filter used for particulate detection with this technology, and the degree of freedom of regenerating operation of the particulate detection filter is restricted.

Further, with the technology of the U.S. Pat. No. 5,651,248, it is not possible to use the diesel particulate filter during the regeneration operation carried out by the heater, and because of this, there is provided a reserve diesel particulate filter and switches to this reserve diesel particulate filter during the regeneration process. However, such a construction requires two equivalent diesel particulate filters together with a switching valve, and there arises a problem in that the construction of the exhaust gas purifying apparatus becomes bulky. It is difficult to mount such an exhaust gas purifying apparatus on compact vehicles.

Further, with the technology of the U.S. Pat. No. 5,651,248, regeneration of the detection filter is carried out concurrently with the diesel particulate filter or consecutively to the diesel particulate filter, while such a construction cannot choose the timing of regeneration of the detection filter arbitrarily, and there is a problem that error tends to be caused in the regeneration timing of the diesel particulate filter, depending upon the state of the detection filter.

When regeneration of the diesel particulate filter and regeneration of the detection filter are carried out independently, there is caused a decrease of ventilation resistance in the detection filter upon regeneration thereof, and the exhaust gas starts to flow primarily through the detection filter. Thereby, there is caused an error in the detection of regeneration timing of the diesel particulate filter. From these reasons, the technology of U.S. Pat. No. 5,651,248 carries out the regeneration of the detection filter and the regeneration of the diesel particulate filter in synchronization as explained before.

Further, the technology of the U.S. Pat. No. 5,651,248 has a drawback in the points of: (a) ash deposition; and (b) large evaluation error caused by deterioration.

Further, with the technology of the U.S. Pat. No. 5,651,248, there arises another problem from the very principle thereof of measuring electric resistance of electrode for evaluating the deposition amount of the collected particulate matter.

As shown in FIGS. 5A, 5B, and 5C, there can be a situation in which the thickness of the collected particulate matter changes in spite of the fact that the deposition amount thereof is the same. Now, when the thickness of the collected particulate matter is different, it becomes difficult to measure the electrical resistance precisely, and there tends to be caused error in the evaluation of the deposition amount.

Further, in the case there is caused a deposition of ash in the diesel particulate filter or detection filter after burning of the particulate matter, no precise measurement of electrical resistance is possible anymore and there should be caused a large error in the evaluation of the deposition amount.

Further, with the use of the detection filter, there tends to be caused degradation in the filter or electrode with time or with use in the ambient of exhaust gas. Particularly, the electrode (terminal formed of a conductive metal) is formed by infiltrating a metal such as Cu, Cr, Ni, or the like, and thus, there is a tendency of causing problems of physical degradation, oxidation degradation and thermal degradation, such as oxidation, adhesion of impurities, cracking, corrosion, and the like.

When there is caused degradation in the filter or electrode, it is no longer possible to carry out precise measurement of the electric resistance and error is tend to be caused in the evaluation of the deposition amount of the particulate matter.

According to the embodiments of the present invention, it becomes possible to measure the deposition amount of particulate matter in the primary diesel particulate filter simply and easily, by using the secondary diesel particulate filter of smaller soot storage capacity and hence less prone to cause non-uniform deposition of the particulate matter and by detecting the deposition of the particulate matter in the primary diesel particulate filter by measuring the differential pressure occurring in such a secondary diesel particulate filter. Thereby, it becomes possible to suppress deterioration of fuel efficiency by excessive post injection. Further, with the embodiment of present invention, it becomes possible to execute the regeneration of the secondary diesel particulate filter independently to the primary diesel particulate filter, and it becomes possible to constantly and precisely measure the deposition amount of the particulate matter in the primary diesel particulate filter by using the secondary diesel particulate filter. Further, it becomes possible to perform precise measurement while eliminating the effect of ash deposition or degradation of the filter or electrode.

Further, with the embodiments of present invention, it becomes possible to avoid concentration of the exhaust gas of the exhaust line 21 to the secondary exhaust line 21A with regeneration of the secondary diesel particulate filter, which is caused as a result of decrease of ventilation resistance of the second exhaust line 21A with the regeneration of the secondary diesel particulate filter, by providing a valve in the secondary exhaust line and controlling the flow rate therein to be constant. Thus, collection of the particulate matter in the primary diesel particulate filter is caused similarly to the secondary diesel particulate filter, and it becomes possible to avoid the deviation caused between the evaluation of the deposition amount of the particulate matter in the primary diesel particulate filter, carried out by the measurement of differential pressure in the secondary diesel particulate filter, and the actual deposition amount of the particulate matter in the primary diesel particulate filter.

First Embodiment

Figure 6:
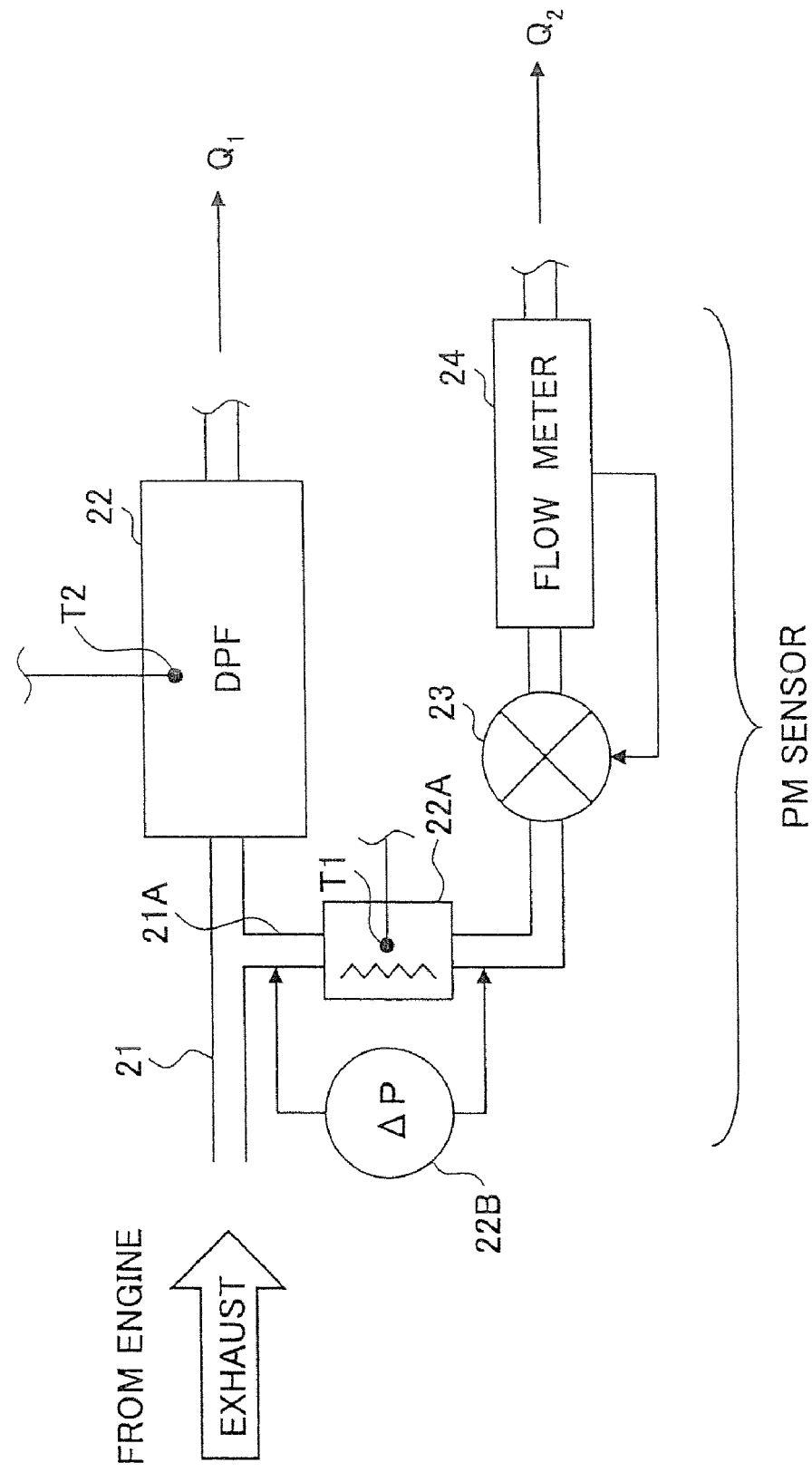
FIG. 6 is a diagram showing the construction of an exhaust gas purifying apparatus according to a first embodiment of the present invention.

FIG. 6 shows the construction of an exhaust gas purifying apparatus 20 according to a first embodiment of the present invention.

Referring to the embodiment of the present invention of FIG. 6, an exhaust gas from a diesel engine not illustrated is caused to flow into a primary diesel particulate filter (DPF) 22 similar to the one explained previously with reference to FIG. 2A via an exhaust line 21, and the primary diesel particulate filter (DPF) 22 collects the particulate matter in the exhaust gas as explained with reference to FIGS. 2C and 2D.

Further, with the construction of the embodiment of the present invention of FIG. 6, a secondary exhaust line 21A is branched from the exhaust line 21 at an upstream side of the primary diesel particulate filter (DPF) 22, and a secondary diesel particulate filter 22A is provided to the secondary exhaust line 21A with a volume smaller than the volume of the primary diesel particulate filter (DPF) 22. Further, there is provided a differential pressure gauge 22B for measuring a differential pressure ΔP caused between an inlet and an outlet of the secondary diesel particulate filter 22A. Further, with the construction of FIG. 6, there are provided a flow meter 24 and a control valve 23 in the secondary exhaust line 21A at a downstream side of the secondary diesel particulate filter 22A, wherein the control valve 23 is used for maintaining the flow rate of the exhaust gas in the secondary exhaust line 21A constant based on the measurement made by the flow meter 24. It should be noted that the control valve 23 and the flow mater 24 may be provided anywhere on the secondary exhaust line 21A. Here, it should be noted that the secondary diesel particulate filter 22A, the differential pressure gauge 22B and the flow meter 24 constitutes together a particulate matter (PM) sensor that measures the amount of particulate contained in the exhaust gas. The particulate matter (PM) sensor may be defined to include a temperature measuring part (T1). Further, it is possible to provide a temperature measurement part T2 in the primary diesel particulate filter (DPF) 22.

It should be noted that the temperature measuring part in the exhaust line may be provided in any of: (1) interior of the primary diesel particulate filter, (2) interior of the secondary diesel particulate filter, (3) in a pipe connected thereto, (4) exterior of the primary diesel particulate filter, or (5) exterior of the secondary diesel particulate filter. From the viewpoint of precise measurement of the exhaust gas temperature, the arrangement of (1) or (2) is preferable, wherein the arrangement of (2) is thought more preferable.

Figure 7A:
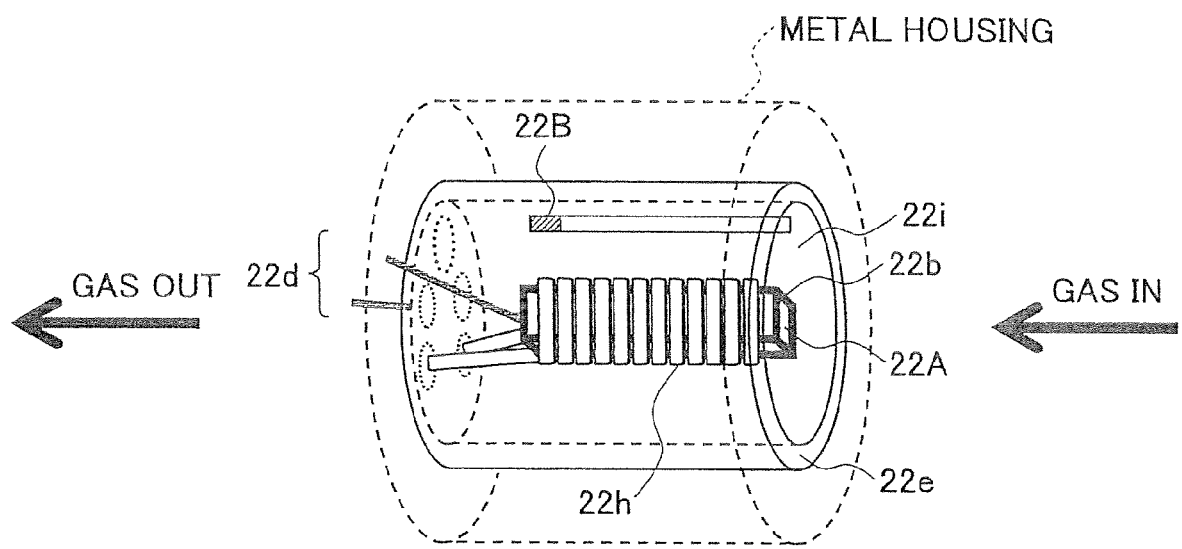
FIG. 7A is a diagram showing the construction of a secondary diesel particulate filter used in FIG. 6.
Figure 7B:
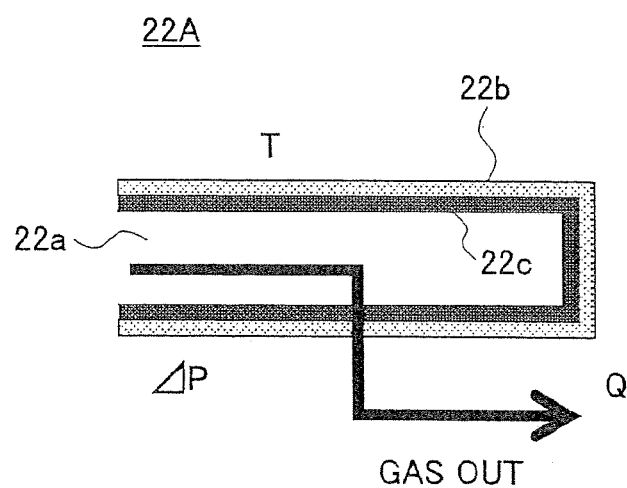
FIG. 7B is a diagram explaining the principle of the secondary diesel particulate filter of FIG. 7A.

FIG. 7A shows the overall construction including the secondary diesel particulate filter 22A, while FIG. 7B shows the principle of the secondary diesel particulate filter 22A.

It should be noted that the secondary diesel particulate filter 22A may be formed of a porous ceramic similar to the primary diesel particulate filter (DPF) 22. In the case the secondary diesel particulate filter is formed of a porous ceramic, it is preferable that the secondary diesel particulate filter includes a cell 22b of a rectangular form. Therein, there is formed a single gas passage 22a having a volume of about 65 ml or less such as about 0.05 to about 65 ml, or about 5% or less such as about 0.05 to about 5% of the total volume of the exhaust gas passages (corresponding to passage 12a of FIG. 3) in the primary diesel particulate filter (DPF) 22. Alternatively, the gas passage 22a may have a filtration area of about 0.1 to about 1000 cm$^2$ (preferably about 1 to about 10 cm$^2$). The gas passage 22a may have a rectangular cross-sectional shape, for example, and is formed in the state that one end thereof is closed (rear end is closed in the case of a cell). Here, it should be noted that the outer shape of the gas passage 22a or the outer shape of the secondary diesel particulate filter 22A (cell 22b) is not necessarily be identical to the cross-sectional shape of the gas passages of the primary diesel particulate filter (DPF) 22, and thus, they can be shaped to any arbitrary shape of circular, square, octahedral, elliptical, or the like. Further, it should be noted that the porous ceramic constituting the secondary diesel particulate filter 22A (cell 22b) is not necessarily be identical with the porous ceramic that forms the primary diesel particular filter (DPF) 22. Further, it should be noted that the secondary diesel particulate filter 22A (cell 22b) may be formed of a material other than ceramics.

By forming the gas passage 22a with the volume of about 5% or less of the exhaust gas passage (corresponds to the passage 12a of FIG. 3) in the primary diesel particulate filter (DPF) 22, or with the volume of 65 ml or less, or with the filtration area of about 0.1 to about 1000 cm$^2$ (preferably about 1 to about 10 cm$^2$), it becomes possible to measure the deposition amount of the particulate matter in the primary diesel particulate filter (DPF) 22 with a simple procedure.

The secondary diesel particulate filter 22A (cell 22b) is provided with a temperature measuring part for measuring the exhaust gas temperature T, and a thermocouple 22d is provided for the temperature measuring part. Further, a heater 22h is wound around the secondary diesel particulate filter (cell 22b) for incinerating a soot layer 22c deposited on the inner wall surface and regenerating the secondary diesel particulate filter 22A. Further, the cell 22b, the thermocouple 22d and the heater 22h are accommodated in a cylindrical holder 22e of SiO$_2$—Al$_2$O$^-$, or the like, by interposing an insulator 22i of Al$_2$O$_3$, or the like, and there is provided a diaphragm pressure gauge 22B in the holder 22e for measuring the differential pressure ΔP, in such a manner that the exhaust gas in the secondary exhaust line 21A is supplied to the pressure gauge 22B. The holder 22e is accommodated in a metal housing and is provided to the secondary exhaust line as the particulate matter (PM) sensor. The holder 22e may also be provided inside the pipe of the secondary exhaust line or may be provided inside the secondary exhaust line in the state accommodated in the metal housing.

Thus, when the exhaust gas in the secondary exhaust line 21A is introduced to the exhaust passage 22a of the secondary diesel particulate filter (cell 22b), the exhaust is caused to flow outside the cell through the wall surface of the secondary diesel particulate filter (cell 22b), and the particulate matter in the exhaust gas is collected similarly to the case of FIG. 2C. Thereby, the particulate matter deposits on the inner surface of the cell 22b to form a layer 22c.

With the present embodiment, the deposition amount of the particulate matter 22c thus collected and deposited on the inner wall surface of the diesel particulate filter 22 is calculated from the pressure difference ΔP and the exhaust gas temperature T and exhaust gas flow rate Q thus obtained by using the equation (1) below.

Figure 8:
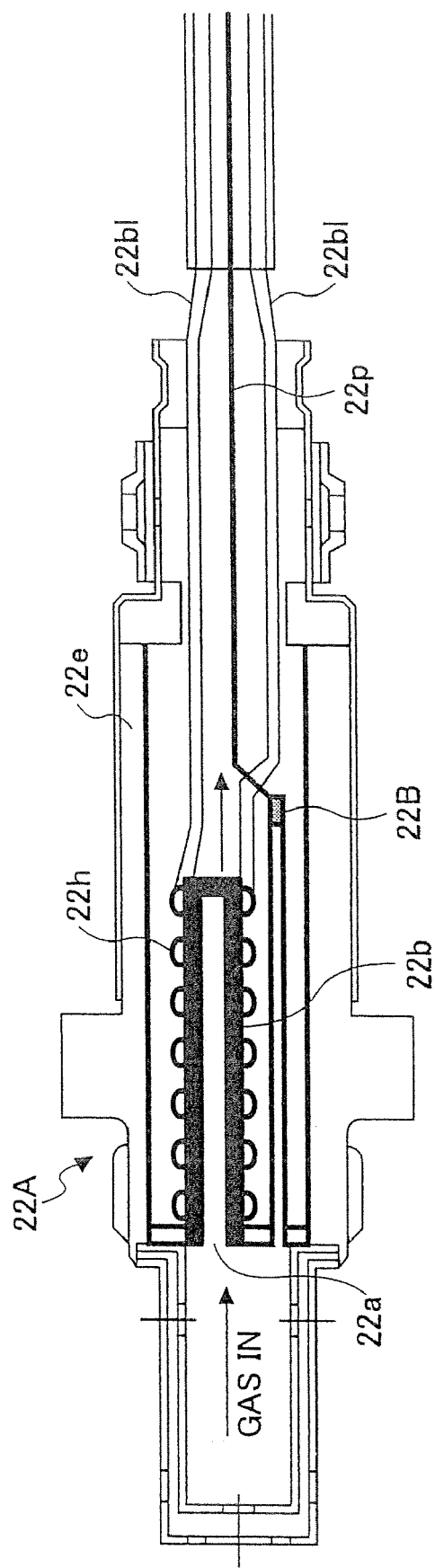
FIG. 8 is a diagram showing the construction of a particulate matter (PM) sensor that uses the secondary diesel particulate filter of FIG. 6.

FIG. 8 shows a more detailed construction of the secondary diesel particulate filter 22A of FIG. 6.

Referring to FIG. 8, the exhaust gas in the secondary exhaust line 21A is supplied to the gas passage 22a in the secondary diesel particulate filter (cell 22b) as represented by an arrow and is discharged, after passing through the cell, in the lateral direction or rear direction. Thereby, the heater 22h on the secondary diesel particulate filter (cell 22b) is driven by the electric power supplied by a drive line 22b1 and causes incineration in the particulate matter 22c collected by the cell 22b. Further, the output signal of the diaphragm pressure gauge 22B is supplied to a control circuit via a signal line 22p.

With the secondary diesel particulate filter 22A of FIGS. 7A and 7B, the amount of soot load of the particulate matter collected in the secondary diesel particulate filter is calculated according to an equation of the form $$\Delta P = \frac{\mu Q}{2V_{trap}}(\alpha + W_s)^2 \left[ \frac{W_s}{K_w \alpha} + \frac{1}{2K_{SOOT}} \ln\left(\frac{\alpha}{\alpha - 2W}\right) + \frac{4FL^2}{3}\left(\frac{1}{(\alpha - 2W)^4} + \frac{1}{\alpha^4}\right)\right] + \frac{\rho Q^2 (\alpha + W_s)^4}{V_{trap}^2}\left[\frac{\beta W_s}{4} + 2\zeta\left[\frac{L}{\alpha}\right]^2\right] \quad (1)$$

wherein ΔP represents the differential pressure [Pa], μ represents a kinetic viscosity coefficient, Q represents the flow rate of the exhaust gas represented in terms of [m³/h], α represents an edge length of the cell, p represents a specific gravity of the exhaust gas, $V_{trap}$ represents a filter volume, Ws represents a wall thickness, Kw represents a wall gas permeability, $K_{soot}$ represents a gas permeability of the collected particulate matter layer, W represents the thickness of the collected particulate matter layer, F is a numerical coefficient (=28.454), L represents an effective filter length, β represents the Forchheimer coefficient of the porous wall, q represents the inertial loss coefficient of the exhaust gas entering and exiting the filter.

Next, the mass $m_{soot}$ of the particulate matter collected by the secondary diesel particulate filter (cell 21b) is obtained according to $$W = \frac{\alpha - \sqrt{\alpha^2 - \frac{m_{soot}}{N_{cells} \times L \times \rho_{soot}}}}{2} \quad (2)$$

wherein $m_{soot}$ represents the mass [g] of the particulate matter collected, while $N_{cells}$ represents an aperture number of the cell at the inlet side, and $\rho_{soot}$ represents the density of the collected particulate matter.

Thus, a collection amount per unit time, PM [g/h] is obtained by dividing $m_{soot}$ by the time [h] as measured from the previous regeneration of the secondary diesel particulate filter 22A.

Once the mass PM [g/h] of the particulate matter deposited in a unit time is obtained, the concentration of the particulate matter in the exhaust gas, $PM_{conc}$ [g/m³], is obtained by using the flow rate Q2 [m³/h] of the exhaust gas passing through the secondary diesel particulate filter 22A as $$PM[g/h] = PM_{conc}[g/m^3] \times Q2[m^3/h]. \quad (3)$$

Because the concentration $PM_{conc}$ of the particulate matter in the exhaust gas takes the same value in the secondary exhaust line 21A and also in the exhaust lien 21, the amount of the particulate matter $PM_{enter\ full\ filter}$ [g/h] that has flowed into the diesel particulate filter 22 is obtained from the mass PM [g/h] of the particulate matter deposited per unit time, as $$PM_{enter\ full\ filter}[g/h] = PM_{conc}[g/m^3] \times Q1[m^3/h] \quad (4)$$

Further, from this, the amount of the particulate matter deposited in the filter is obtained by taking into consideration the collection efficiency of the filter. In the foregoing, Q1 represents the flow rate of the exhaust gas passing through the primary diesel particulate filter (DPF) 22. Q1 may be obtained by actual measurement or estimated from the operational state of the engine.

Figure 9:
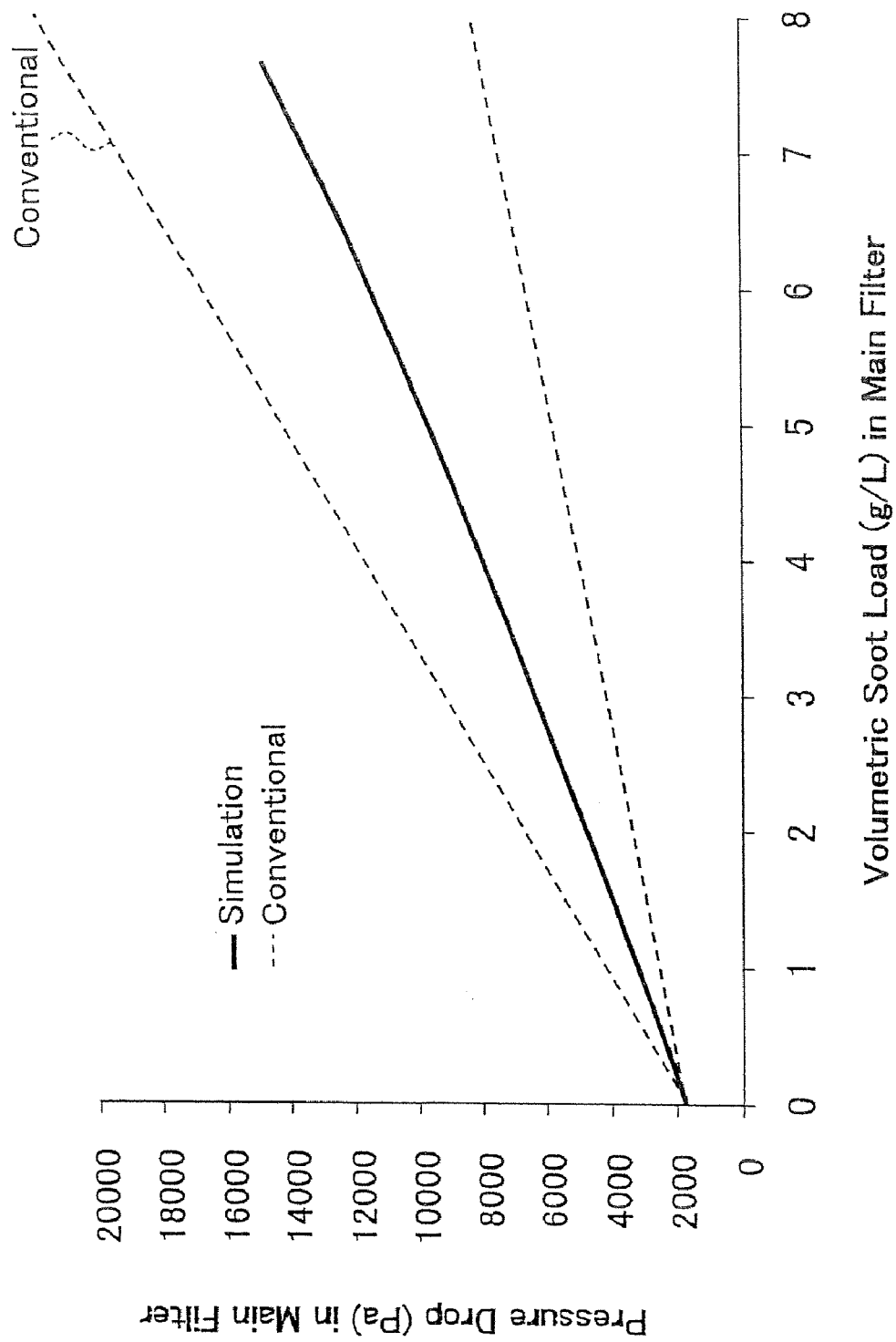
FIG. 9 is a diagram explaining the effect of the embodiment of the invention.

FIG. 9 shows the relationship between the differential pressure occurring across the primary diesel particulate filter (DPF) 22 of the exhaust gas purifying apparatus of the embodiment of FIG. 6 and the deposition amount of the particulate matter in the primary diesel particulate filter (DPF) 22, wherein it should be noted that the continuous line shows the case in which the deposition amount of the particulate matter in the main diesel particulate filter 22 is obtained by using the secondary diesel particulate filter 22A and Equations (1) to (4). On the other hand, the dotted line represents the case in which the deposition amount of the particulate matter in the primary diesel particulate filter (DPF) 22 is obtained directly from the differential pressure across the primary diesel particulate filter (DPF) 22.

Referring to FIG. 9, it can be seen that there can occur a variation, and hence error, of as much as about ±50% in the differential pressure across the primary diesel particulate filter (DPF) 22 when compared at the same deposition amount of the particulate matter.

Contrary to this, it is possible to obtain the amount of deposition of the particulate matter collected by the primary diesel particulate filter (DPF) 22 within the error of about ±10% by obtaining the differential pressure ΔP across the secondary diesel particulate matter and by using Equations (1) to (4).

Thus, according to the embodiment of the present invention, it becomes possible to evaluate the deposition amount of the particulate matter in the primary diesel particulate filter (DPF) 22 in the exhaust gas purifying apparatus of the embodiment of FIG. 6 precisely by measuring the differential pressure ΔP formed in the secondary diesel particulate filter 22A of small volume, and it becomes possible to execute the regeneration of the primary diesel particulate filter (DPF) 22 with optimum timing by way of carrying out the post injection based on the foregoing result. With this, unnecessary post injection is avoided and the fuel efficiency of the vehicle is improved.

In the construction of the embodiment of FIG. 6, it is possible to use a known Vencheri flow meter, hotwire flow meter, or the like, wherein the flow meter 24 can control the exhaust gas flow rate in the secondary exhaust line 21A generally constant within the range of about 50 to about 6000 ml/min, for example. With this, one-sided flow of the exhaust gas through the secondary exhaust line 21A is avoided, and it becomes possible to obtain the deposition amount of the particulate matter in the primary diesel particulate filter (DPF) 22 from the deposition amount obtained by using the secondary diesel particulate filter 22A, with further improved precision.

Here, it should be noted that the "differential pressure measuring part measuring a differential pressure between an inlet and an outlet of said secondary diesel particulate filter" includes not only the differential pressure gauge that measures the differential pressure between the inlet side and the outlet side of the secondary diesel particulate filter 22A but also the construction that uses a pressure gauge only at the outlet side of the diesel particulate filter 22A. With such a construction, the pressure value of the initial state (the state immediately after regeneration) is memorized and the differential pressure is calculated by measuring the pressure for the state in which there occurred deposition of the particulate material in the secondary diesel particulate filter 22A and by subtracting the pressure value thus obtained from the memorized initial pressure value.

Further, it is also possible to provide a flow meter, a flow velocity meter, or the like, at the inlet side and the outlet side or only at the outlet side of the secondary diesel particulate filter for measuring the differential pressure. With such a construction, the differential pressure is obtained from the reading value of the flow meter, flow velocity meter, or the like, provided at the inlet side and the outlet side of the secondary diesel particulate filter. Alternatively, the differential pressure may be obtained from the reading value of the flow meter, the flow velocity meter, or the like, at the outlet side of the secondary diesel particulate filter, by comparing the reading value for the initial state (the state immediately after regeneration) and the reading value for the state where there is caused deposition of the particulate matter in the secondary diesel particulate filter.

The embodiment of the present invention has the feature of obtaining the amount of the particulate matter deposited in the primary diesel particulate filter (DPF) 22 from the differential pressure obtained for the secondary diesel particulate filter 22A by using Equations (1) to (4), and thus, any instruments including those that are used conventionally for measuring a differential pressure may be used for measuring the differential pressure of the secondary diesel particulate filter.

Second Embodiment

Figure 10:
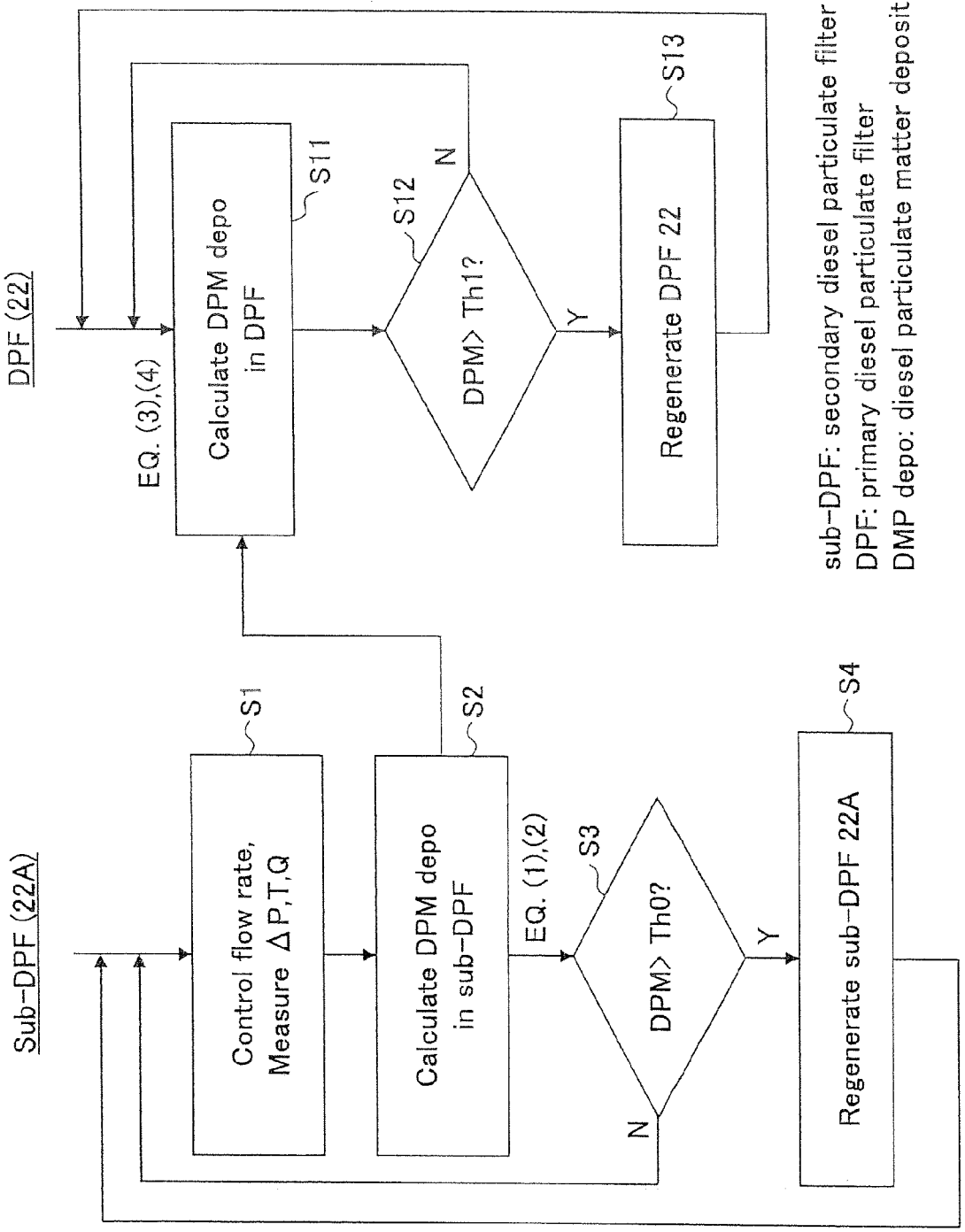
FIG. 10 is a flow chart explaining the regeneration operation of the diesel particulate filter in the exhaust gas purifying apparatus according to a second embodiment of the present invention.

FIG. 10 is a flowchart showing the exhaust gas purifying method according to a second embodiment of the present invention that uses the exhaust gas purifying apparatus of the embodiment of FIG. 6.

Referring to FIG. 10, the exhaust gas flow rate Q is detected by the flow meter 24 in the step 1 and the differential pressure $\Delta P$ across the secondary diesel particulate filter 22A is detected by the differential pressure gauge 22B. Further, the temperature of the exhaust gas is detected by using the temperature measuring part T1.

Next, in the step 2, the layer thickness W of the particulate matter collected by the secondary diesel particulate filter 22A is obtained from the differential pressure $\Delta P$ detected in the step 1 according to Equation (1). Here, it should be noted that the temperature T of the exhaust gas may be obtained by using the temperature measuring part T2 of the primary diesel particulate filter (DPF) 22 in place of using the temperature measuring part T1 of the secondary diesel particulate filter 22A as in the present case. Further, the temperature T may be calculated from the temperatures of the temperature measuring parts T1 and T2 (in the form of average value, maximum value, minimum value, for example). From the viewpoint of calculating the amount of the particulate matter more precisely, it is preferable to use the temperature measuring part T1 of the secondary diesel particulate filter 22A. For the temperature measuring part, a thermocouple may be used, while it is also possible to use anything as long as it can measure the temperature. While it is preferable to measure the temperature of the exhaust gas inside the exhaust pipe, it is also possible to measure the temperature of the filter or the cell.

Further, in the step 2, the mass $m_{soot}$ of the particulate matter collected by the cell 21b is obtained from the layer thickness W detected in the step 1 by using Equation (2) mentioned previously.

Further, in the step 3, it is judged whether or not the mass $m_{soot}$ of the layered particulate matter deposited in the cell 22b of the secondary diesel particulate filter 22A has exceeded a predetermined threshold Th0, and if the result is NO, the process returns to the step 1.

When the mass $m_{soot}$ of the layered particulate matter deposited in the cell 22b of the secondary diesel particulate filter 22A has exceeded the predetermined threshold Th0 in the step 3, the heater 22h is activated in the step 4 and the particulate matter 22c is removed by burning.

Meanwhile, in the process of FIG. 10, the concentration PM of the particulate matter in the exhaust gas is obtained in the step 11 from Equation (3) while using the mass $m_{soot}$ of the collected particulate matter in the cell 22b obtained in the step 2, and the deposited amount $PM_{enter\,full\,filter}$ of the particulate deposited in the principal diesel particulate filter 22 is obtained from Equation (4) and from the collection efficiency of the primary diesel particulate filter (DPF) 22.

Thus, in the step 12, it is judged whether or not the deposited amount $PM_{enter\,full\,filter}$ of the particulate matter in the primary diesel particulate filter (DPF) 22 exceeds a predetermined threshold value Th1, and if the result of judgment is NO, the operation returns to the step S11.

In the event it is judged in the step 12 that the deposited amount $PM_{enter\,full\,filter}$ of the particulate matter in the primary diesel particulate filter (DPF) 22 exceeds the predetermined threshold value Th1, post injection is executed in the step 13 by controlling an engine control unit (ECU), and the deposited particulate matter in the primary diesel particulate filter (DPF) 22 is removed by burning. Thereby, regeneration of filter is achieved.

With the process of FIG. 10, it is possible to carry out the regeneration of the secondary diesel particulate filter 22A and the primary diesel particulate filter (DPF) 22 independently, and thus, it is possible to always maintain the deposited amount of the particulate matter 22c, or the amount of the soot layer, in the cell 22b, which constitutes the secondary diesel particulate filter 22A, to be a small value of about 0.5 g/l or less. With such a construction, it becomes possible to improve the sensitivity of the particulate matter sensor that uses the secondary diesel particulate filter 22A.

With the construction of the embodiment of FIG. 6, in which the valve 23 is inserted into the secondary exhaust line 21A, there is caused no such a situation that the exhaust gas flows predominantly through the secondary diesel particulate filter where regeneration has been made even when the regeneration of the secondary diesel particulate filter 22A is conducted independently to the primary diesel particulate filter (DPF) 22, and there is caused no error in the evaluation of the deposited amount of the particulate matter in the primary diesel particulate filter (DPF) 22.

Thereby, it should be noted that there is no need for the valve 23 to maintain the exhaust gas flow rate in the secondary exhaust line 21A exactly at a constant level but it is just sufficient to avoid extreme deviation of the exhaust gas flow to the secondary exhaust line 21A.

Thus, in the second embodiment noted above, the differential pressure $\Delta P$, the exhaust gas temperature T and the exhaust gas flow rate Q are measured (step 1), the mass of the particulate matter collected by the secondary diesel particulate filter is obtained by using Equations (1) and (2) from the foregoing result of measurement (step 2), and the amount of the particulate matter collected by the primary diesel particulate filter is obtained from the amount of the particulate matter collected in the secondary diesel particulate filter by using Equations (3) and (4) and further using the collection efficiency of the primary diesel particulate filter (step 11).

In FIG. 10, and also in FIG. 11 to be explained below, the primary diesel particulate filter (DPF) 22 is designated as DPF while the secondary diesel particulate filter 22A is designated as sub-DPF. Further, the deposition of diesel particulate matter is designated as DPM depo.

Figure 11:
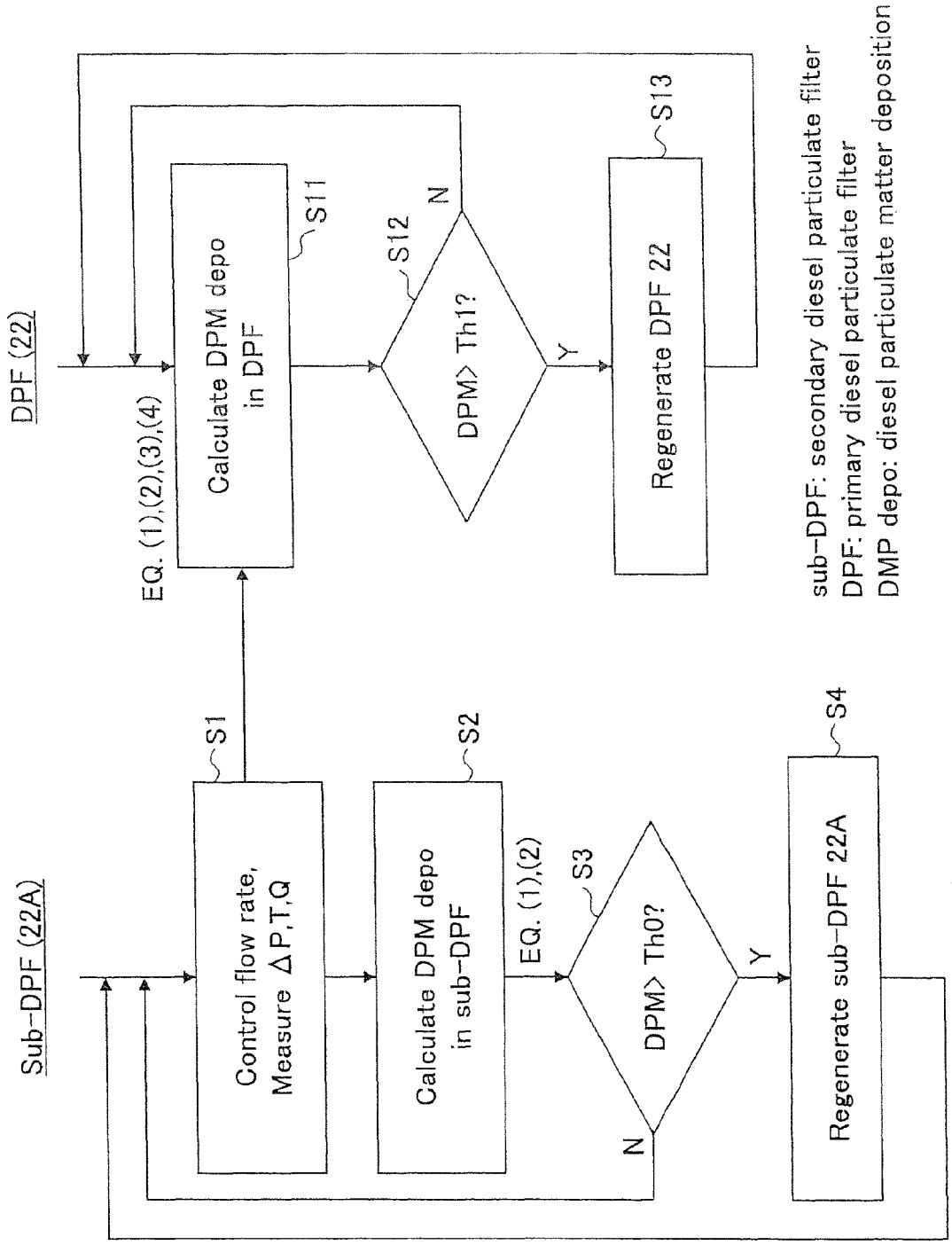
FIG. 11 is a flowchart explaining another regeneration operation of the diesel particulate filter of the exhaust gas purifying apparatus according to the second embodiment of the present invention.

On the other hand, the process of obtaining the amount of the particulate matter collected in the primary diesel particulate filter may be modified as shown in FIG. 11.

Thus, in FIG. 11, the process for obtaining the amount of the particulate matter collected by the primary diesel particulate filter (step 11) is carried out in parallel with the process of obtaining the amount of the particulate matter collected by the secondary diesel particulate filter (step 2), while using the result of measurement obtained in the step 1.

Third Embodiment

Figure 12:
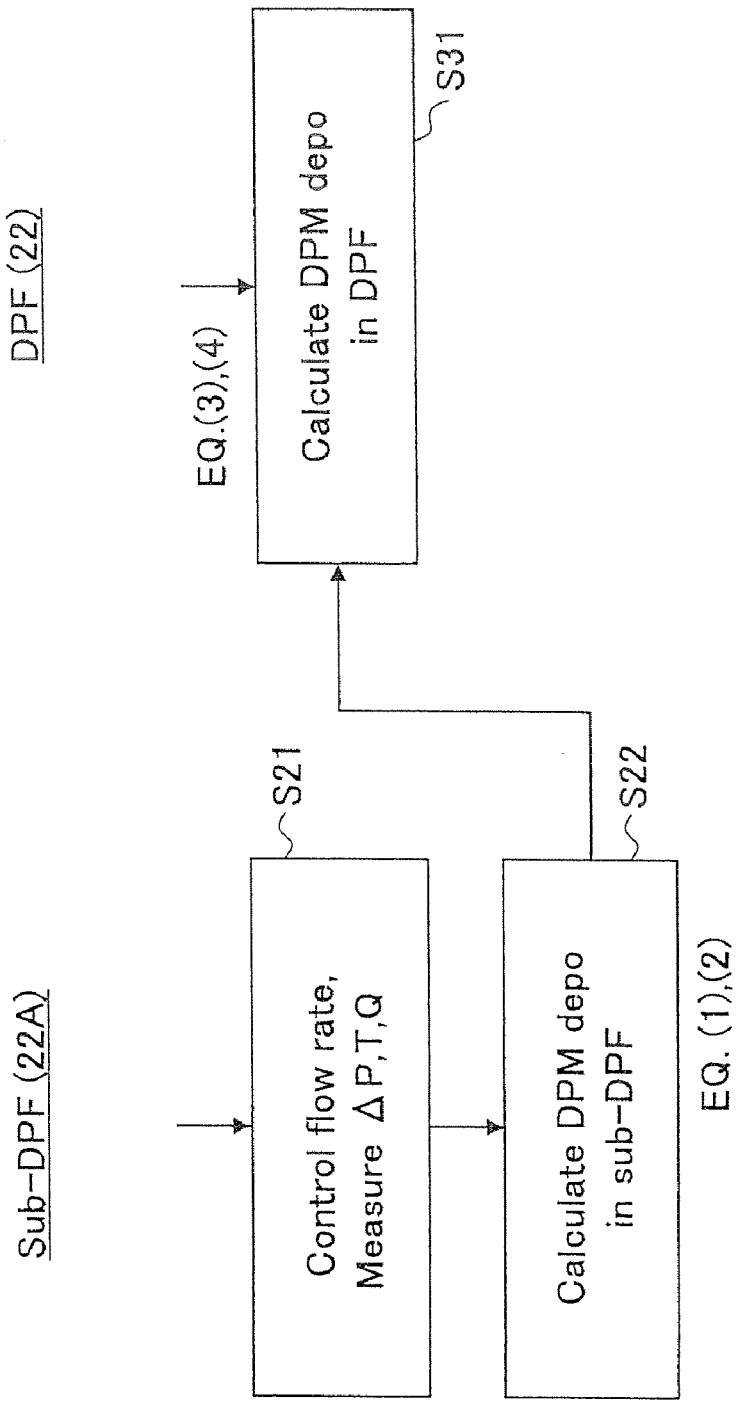
FIG. 12 is a flowchart showing the particulate matter measuring method according to the steps A-D of FIG. 10.

FIG. 12 is a flowchart showing the particulate matter measuring method according to a third embodiment of the present invention that uses the particulate matter sensor PM of the embodiment of FIG. 6, wherein those parts corresponding to the parts described previously are designated by the same reference numerals and the description thereof will be omitted.

Referring to FIG. 12, the flow rate in the secondary exhaust line 21A is set to a predetermined value in the range of about 50 to about 6000 ml/min in the step 21 corresponding to the foregoing step 1 by using the flow meter 24, or in some cases by using the valve 23, and the differential pressure ΔP across the secondary diesel particulate filter 22A is detected by the differential pressure gauge 22B. Further, the temperature of the exhaust gas is detected by using the temperature measuring part T1.

Next, in the step 22 corresponding to the foregoing step 2, the layer thickness W of the particulate matter collected by the secondary diesel particulate filter 22A is obtained from the differential pressure ΔP detected in the step 1 according to Equation (1) Here, it should be noted that the temperature T of the exhaust gas may be obtained by using the temperature measuring part T2 of the primary diesel particulate filter (DPF) 22 in place of using the temperature measuring part T1 of the secondary diesel particulate filter 22A as in the present example. Further, the temperature T may be calculated from the temperatures of the temperature measuring parts T1 and T2 (in the form of average value, maximum value, minimum value, for example). From the viewpoint of calculating the amount of the particulate matter more precisely, it is preferable to use the temperature measuring part Ti of the secondary diesel particulate filter 22A. For the temperature measuring part, a thermocouple may be used, while it is also possible to use anything as long as it can measure the temperature. While it is preferable to measure the temperature of the exhaust gas inside the exhaust pipe, it is also possible to measure the temperature of the filter or the cell.

Further, in the step 22, the mass $m_{soot}$ of the particulate matter collected by the cell 21b is obtained from the layer thickness W detected in the step 1 by using Equation (2) mentioned previously.

Further, in the process of FIG. 12, the concentration PM of the particulate matter in the exhaust gas is obtained in the step 31 corresponding to the foregoing step 11 from Equation (3) while using the mass $m_{soot}$ of the collected particulate matter in the cell 22b obtained in the step 22, and the deposited amount $PM_{enter\_full\_filter}$ of the particulate deposited in the principal diesel particulate filter 22 is obtained from Equation (4) and from the collection efficiency of the primary diesel particulate filter (DPF) 22.

Thus, in the third embodiment noted above, the differential pressure ΔP, the exhaust gas temperature T and the exhaust gas flow rate Q are measured (step 21), the mass of the particulate matter collected by the secondary diesel particulate filter is obtained by using Equations (1) and (2) from the foregoing result of measurement (step 22), and the amount of the particulate matter collected by the primary diesel particulate filter is obtained from the amount of the particulate matter collected in the secondary diesel particulate filter by using Equations (3) and (4) and further using the collection efficiency of the primary diesel particulate filter (step 31).

In FIG. 12, and also in FIG. 13 to be explained below, the primary diesel particulate filter (DPF) 22 is designated as DPF while the secondary diesel particulate filter 22A is designated as sub-DPF. Further, the deposition of diesel particulate matter is designated as DPM depo.

Figure 13:
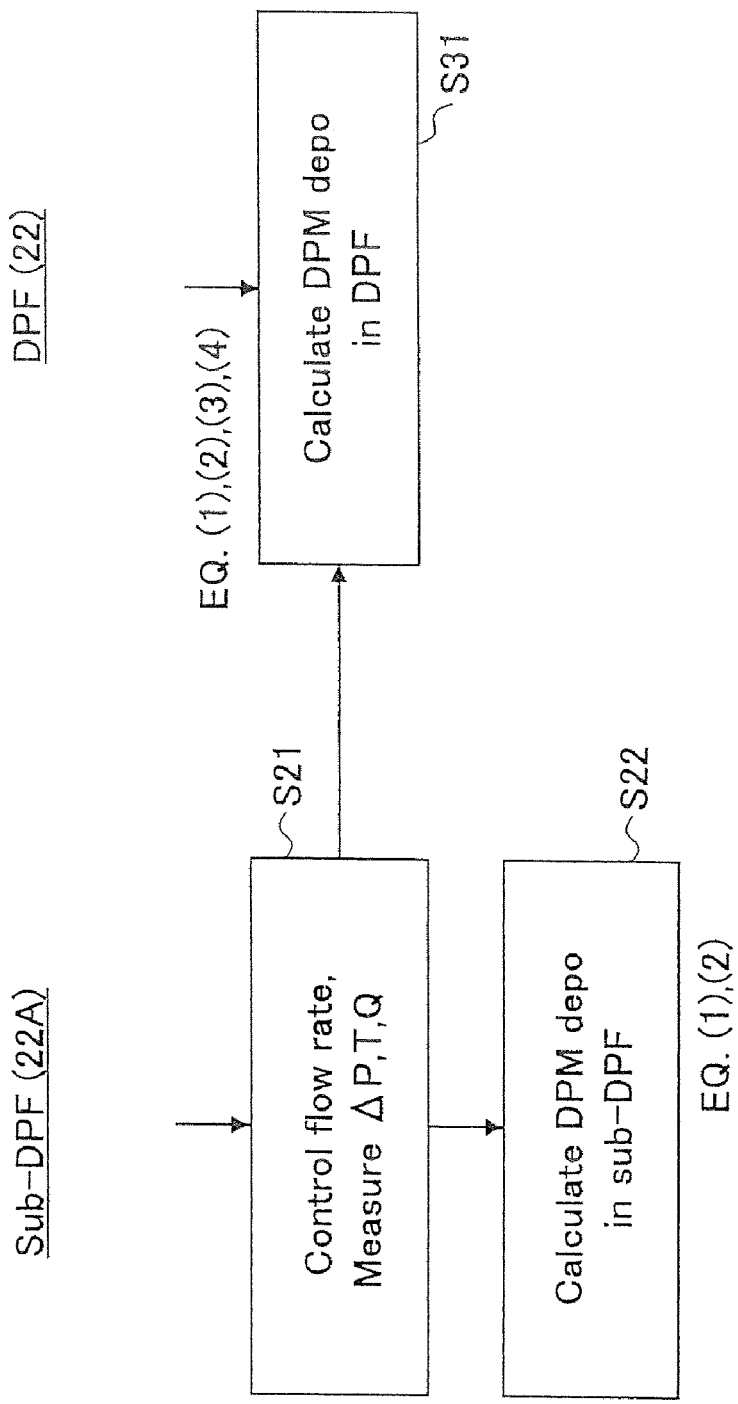
FIG. 13 is a flowchart showing the particulate measuring method according to the steps A-D of FIG. 11.

On the other hand, the process of obtaining the amount of the particulate matter collected in the primary diesel particulate filter may be modified as shown in FIG. 13.

Thus, in FIG. 13, the process for obtaining the amount of the particulate matter collected by the primary diesel particulate filter (step 31) is carried out in parallel with the process of obtaining the amount of the particulate matter collected by the secondary diesel particulate filter (step 22), while using the result of measurement obtained in the step 21.

Further, while the explanation heretofore has been made for the case of using a honeycomb component of SiC for the primary diesel particulate filter (DPF) 22 and the secondary diesel particulate filter 22A, the embodiment of the present invention is by no means limited to such particular filter components, and it is also possible to use a composite material containing silicon carbide by about 60% or more, such as a composite of silicon carbide and metal such as silicon (in the present invention such a composite should also be referred to as silicon carbide), a nitride such as aluminum nitride, silicon nitride, boron nitride, tungsten nitride, or the like, a carbide such as Zirconium carbide, titanium carbide, tantalum carbide, tungsten carbide, or the like, an oxide such as alumina, zirconium oxide, cordierite, mullite, silica, aluminum titanate, or a porous body of metal such as stainless steel. Further, it is possible to use a structural body such as corrugate or element plate in addition to the honeycomb structure.

The exhaust gas purifying apparatus of the embodiment of the present invention has a compact size and is applicable not only to large vehicles such as trucks or industrial machines but also to passenger cars.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. An exhaust gas purifying apparatus, comprising:
   a primary diesel particulate filter provided in an exhaust line of a diesel engine;
   a secondary exhaust line branched from said exhaust line from an upstream side of said primary diesel particulate filter;

a secondary diesel particulate filter provided in said secondary exhaust line, said secondary diesel particulate filter having a soot storage capacity smaller than the soot storage capacity of said primary diesel particulate filter; and a differential pressure measuring part measuring a differential pressure between an inlet and an outlet of said secondary diesel particulate filter.

2. The exhaust gas purifying apparatus as claimed in claim 1, wherein said secondary exhaust line further includes a flow meter.

3. The exhaust gas purifying apparatus as claimed in claim 1, wherein said secondary exhaust line further includes a temperature measuring part.

4. The exhaust gas purifying apparatus as claimed in claim 1, wherein said secondary diesel particulate filter includes a heater.

5. The exhaust gas purifying apparatus as claimed in claim 1, further including a valve for maintaining a flow rate of said exhaust gas in said secondary exhaust line at a predetermined value.

6. An exhaust gas purifying method that uses an exhaust gas purifying apparatus comprising: a primary diesel particulate filter provided in an exhaust line of a diesel engine; a secondary exhaust line branched from said exhaust line from an upstream side of said primary diesel particulate filter; a secondary diesel particulate filter provided in said secondary exhaust line, said secondary diesel particulate filter having a soot storage capacity smaller than the soot storage capacity of said primary diesel particulate filter; and a differential pressure measuring part measuring a differential pressure between an inlet port and an outlet port of said secondary diesel particulate filter, said exhaust gas purifying method comprising the steps of:

(A) measuring a differential pressure caused across said secondary diesel particulate filter, a temperature of an exhaust gas in said secondary exhaust line, and a flow rate of said exhaust gas;

(B) calculating the mass of particulate matter collected by said secondary diesel particulate filter per unit time from said differential pressure, said temperature and said flow rate of said exhaust gas obtained in said step (A);

(C) calculating the concentration of said particulate matter in said exhaust gas from said mass of particulate matter collected by said secondary diesel particulate filter per unit time obtained in said step (B);

(D) calculating the mass of said particulate matter flowed into said primary diesel particulate filter from said concentration of said particulate matter in said exhaust gas obtained in said step (C) and further from a state of engine operation or a gas flow rate to said primary diesel particulate filter;

(E) judging whether or not said mass of said particulate matter collected by said primary diesel particulate filter has exceeded a predetermined threshold from said mass of said particulate matter collected by said primary diesel particulate filter obtained in said step (D) and a collection efficiency of said primary diesel particulate filter; and (F) executing regeneration of said primary diesel particulate filter in the event said mass of said diesel particulate matter collected by said primary diesel particulate filter has exceeded said predetermined threshold.

7. The exhaust gas purifying method as claimed in claim 6, further including the step of regenerating said secondary diesel particulate filter, regeneration of said secondary diesel particulate filter being executed independently to regeneration of said primary diesel particulate filter in the case when a mass of particulate matter collected in said secondary diesel particulate filter has exceeded a predetermined value.

8. The exhaust gas purifying method as claimed in claim 7, wherein said step of regenerating said secondary diesel particulate filter is executed, after said step (A), by a first process that includes said step (B), and wherein said step of regenerating said primary diesel particulate filter is executed, after said step (B) of said first process, by a second process that includes said steps (C) and (D).

9. The exhaust gas purifying method as claimed in claim 7, wherein said step of regenerating said secondary diesel particulate filter is executed, after said step (A), by a first process that includes said step (B), and wherein said step of regenerating said primary diesel particulate filter is executed, after said step (A), by a second process that includes said steps (B) to (D), wherein said first process and said second process are executed in parallel.

10. The exhaust gas purifying method as claimed in claim 6, wherein said step (B) calculates a thickness W[m] of a layer of said particulate matter collected in said secondary diesel particulate filter according to an equation of $$\Delta P = \frac{\mu Q}{2V_{trap}}$$

$$(\alpha + W_s)^2 \left[ \frac{W_s}{K_w \alpha} + \frac{1}{2K_{SOOT}} \ln\left(\frac{\alpha}{\alpha - 2W}\right) + \frac{4FL^2}{3}\left(\frac{1}{(\alpha - 2W)^4} + \frac{1}{\alpha^4}\right) \right] +$$

$$\frac{\rho Q^2 (\alpha + W_s)^4}{V_{trap}^2} \left[ \frac{\beta W_s}{4} + 2\zeta \left[\frac{L}{\alpha}\right]^2 \right]$$

wherein $\Delta P$ represents said differential pressure [Pa], $\mu$ represents a kinetic viscosity coefficient, Q represents said flow rate of said exhaust gas in said second diesel particulate filter represented in terms of [m³/h], $\alpha$ represents an edge length of a cell in said secondary diesel particulate filter, $\rho$ represents a specific gravity of said exhaust gas, $V_{trap}$ represents a filter volume of said secondary diesel particulate filter, Ws represents a wall thickness of said secondary diesel particulate filter, Kw represents a well permeability of said secondary diesel particulate filter, $K_{soot}$ represents a permeability of said layer of said particulate matter collected in said second diesel particulate filter, F is a numerical coefficient (=28.454), L represents an effective filter length of said second diesel particulate filter, $\beta$ represents the Forchheimer coefficient of a porous wall of said second diesel particulate filter, ç represents the inertial loss coefficient of said exhaust gas entering and exiting said secondary diesel particulate filter, and further obtains a mass $m_{soot}$ [g] of said particulate matter collected in said secondary diesel particulate filter according to an equation $$W = \frac{\alpha - \sqrt{\alpha^2 - \frac{m_{soot}}{N_{cells} \times L \times \rho_{soot}}}}{2}$$

wherein $N_{cells}$ represents an aperture number of said cell at an inlet side thereof, and psoot represents a density of said collected particulate matter.

11. The exhaust gas purifying method as claimed in claim 10, wherein said step (C) calculates a concentration $PM_{conc}$ [g/m³] of said particulate matter in said exhaust gas by an equation $$PM[g/h]=PM_{conc}[g/m^3] \times Q2[m^3/h]$$

wherein Q2 [m³/h] represents a flow rate of said exhaust gas passing through said secondary diesel particulate filter, PM [g/h] represents the mass of the particulate matter deposited per unit time.

12. The exhaust gas purifying method as claimed in claim 11, wherein said step (D) calculates the amount ($PM_{enter\ full\ filter}$ [g/h]) of said particulate matter flowed into said primary diesel particulate filter by an equation $$PM_{enter\ full\ filter}[g/h]=PM_{conc}[g/m^3] \times Q1[m^3/h]$$

where $PM_{conc\ [g/m^3]}$ represents a concentration of particulate matter in said exhaust gas, and Q1 is a flow rate of said exhaust gas passing through said primary diesel particulate filter.

13. A particulate matter measuring method that uses a particulate matter sensor, said particulate matter sensor comprising: a PM detection filter provided in a gas line branched from an exhaust line of a diesel engine from an upstream side of a diesel particulate filter provided in said exhaust line, said PM detection filter having a soot storage capacity smaller than the soot storage capacity of said diesel particulate filter; and a differential pressure measuring part measuring a differential pressure between an inlet port and an outlet port of said PM detection filter, said particulate matter measuring method comprising the steps of:
 (A) measuring a differential pressure caused across said PM detection filter, a temperature of an exhaust gas in said gas line, and a flow rate of said exhaust gas in said gas line;
 (B) calculating the mass of particulate matter collected by said PM detection filter per unit time from said differential pressure, said temperature and said flow rate of said exhaust gas obtained in said step (A);
 (C) calculating the concentration of said particulate matter in said exhaust gas from said mass of particulate matter collected by said PM detection filter per unit time obtained in said step (B);
 (D) calculating the mass of said particulate matter flowed into said primary diesel particulate filter from said concentration of said particulate matter in said exhaust gas obtained in said step (C) and further from a state of engine operation or a gas flow rate to said primary diesel particulate filter.

14. The particulate matter measuring method as claimed in claim 13, wherein said step of obtaining the mass of said particulate matter collected by said PM detection filter is executed, after said step (A), by a first process that includes said step (B), and wherein said step of obtaining the mass of said particulate matter flowed into said diesel particulate filter is executed, after said step (B) of said first process, by a second process that includes said steps (C) and (D).

15. The particulate measuring method as claimed in claim 13, wherein said step of obtaining the mass of said particulate matter collected by said PM detection filter is executed, after said step (A), by a first process that includes said step (B), and wherein said step of obtaining the mass of said particulate matter flowed into said diesel particulate filter is executed, after said step (A), by a second process that includes said steps (B) to (D), wherein said first process and said second process are executed in parallel.

16. The particulate matter measuring method as claimed in claim 13, wherein said step (B) obtains a thickness W[m] of a layer of said particulate matter collected in said PM detection filter according to an equation of $$\Delta P = \frac{\mu Q}{2V_{trap}}(\alpha + W_s)^2 \left[\frac{W_s}{K_w \alpha} + \frac{1}{2K_{SOOT}}\ln\left(\frac{\alpha}{\alpha - 2W}\right) + \frac{4FL^2}{3}\left(\frac{1}{(\alpha-2W)^4} + \frac{1}{\alpha^4}\right)\right] + \frac{\rho Q^2 (\alpha + W_s)^4}{V_{trap}^2}\left[\frac{\beta W_s}{4} + 2\zeta\left[\frac{L}{\alpha}\right]^2\right]$$

wherein ΔP represents said differential pressure [Pa], μ represents a kinetic viscosity coefficient, Q represents said flow rate of said exhaust gas in said PM detection filter represented in terms of [m³/h], α represents an edge length of a cell in said PM detection filter, ρ represents a specific gravity of said exhaust gas, $V_{trap}$ represents a filter volume of said PM detection filter, Ws represents a wall thickness of said PM detection filter, Kw represents a well permeability of said PM detection filter, $K_{soot}$ represents a permeability of said layer of said particulate matter collected in said PM detection filter, F is a numerical coefficient (=28.454), L represents an effective filter length of said PM detection filter, β represents the Forchheimer coefficient of a porous wall of said PM detection filter, ç represents the inertial loss coefficient of said exhaust gas entering and exiting said PM detection filter, and further obtains a mass $m_{soot}$ [g] of said particulate matter collected in said PM detection filter according to an equation $$W = \frac{\alpha - \sqrt{\alpha^2 - \frac{m_{soot}}{N_{cells} \times L \times \rho_{soot}}}}{2}$$

wherein $N_{cells}$ represents an aperture number of said cell at an inlet side thereof, and $\rho_{soot}$ represents a density of said collected particulate matter.

17. The particulate matter measuring method as claimed in claim 16, wherein said step (C) calculates a concentration $PM_{conc}$ [g/m³] of said particulate matter in said exhaust gas by an equation $$PM[g/h]=PM_{conc}[g/m^3] \times Q2[m^3/h]$$

wherein Q2 [m³/h] represents a flow rate of said exhaust gas passing through said PM detection filter, PM [g/h] represents the mass of the particulate matter deposited per unit time in said PM detection filter.

18. The particulate matter measuring method as claimed in claim 17, wherein said step (D) calculates the amount ($PM_{enter\ full\ filter}$ [g/h]) of said particulate matter flowed into said primary diesel particulate filter by an equation $$PM_{enter\ full\ filter}[g/h]=PM_{conc}[g/m^3] \times Q1[m^3/h]$$

where $PM_{conc}$ [g/m³] represents a concentration of particulate matter in said exhaust gas, and Q1 is a flow rate of said exhaust gas passing through said primary diesel particulate filter.

19. The exhaust gas purifying apparatus as claimed in claim 1, wherein said secondary exhaust line does not include a flow control value upstream of said secondary particulate filter.

* * * * *